United States Patent
Poglitsch et al.

(10) Patent No.: US 10,295,552 B2
(45) Date of Patent: *May 21, 2019

(54) METHOD FOR DIAGNOSIS OF PRIMARY HYPERALDOSTERONISM

(71) Applicant: ATTOQUANT DIAGNOSTICS GMBH, Vienna (AT)

(72) Inventors: Marko Poglitsch, Vienna (AT); Cornelia Schwager, Vienna (AT); Dunja Van Oyen, Vienna (AT); Martin Leitner, Graz (AT)

(73) Assignee: ATTOQUANT DIAGNOSTICS GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,433

(22) Filed: Oct. 20, 2017

(65) Prior Publication Data

US 2018/0164330 A1 Jun. 14, 2018

Related U.S. Application Data

(63) Continuation of application No. 15/030,339, filed as application No. PCT/EP2014/072339 on Oct. 17, 2014, now Pat. No. 9,829,496.

(30) Foreign Application Priority Data

| Oct. 18, 2013 | (EP) | 13189386 |
| Jan. 28, 2014 | (EP) | 14152763 |

(51) Int. Cl.
| G01N 33/50 | (2006.01) |
| G01N 33/74 | (2006.01) |
| A61K 31/165 | (2006.01) |
| A61K 31/401 | (2006.01) |
| A61K 31/4178 | (2006.01) |
| G01N 33/49 | (2006.01) |

(52) U.S. Cl.
CPC ......... *G01N 33/743* (2013.01); *A61K 31/165* (2013.01); *A61K 31/401* (2013.01); *A61K 31/4178* (2013.01); *G01N 33/492* (2013.01); *G01N 33/74* (2013.01); *G01N 2333/723* (2013.01); *G01N 2410/02* (2013.01); *G01N 2800/04* (2013.01)

(58) Field of Classification Search
None
See application file for complete search history.

(56) References Cited

U.S. PATENT DOCUMENTS

| 3,919,407 | A | * | 11/1975 | Fernandez de Castro | C12Q 1/37 435/13 |
| 5,420,016 | A | | 5/1995 | Boguslaski | |
| 9,829,496 | B2 | * | 11/2017 | Poglitsch | G01N 33/74 |

| 2006/0019888 | A1 | | 1/2006 | Zhou | |
| 2010/0137420 | A1 | | 6/2010 | Nath | |
| 2010/0311095 | A1 | * | 12/2010 | Bieglmayer | G01N 33/5091 435/21 |

FOREIGN PATENT DOCUMENTS

| CN | 102586223 | 7/2012 |
| JP | H02-2935 | 1/1990 |
| WO | WO 2007/137980 | 12/2007 |
| WO | WO 2008/103420 | 8/2008 |
| WO | WO 2013/134472 | 9/2013 |

OTHER PUBLICATIONS

Schalekamp et al., Angiotensin II production and distribution in the kidney: I. A kinetic model, Kidney International, 2006, 69, pp. 1543-1552. (Year: 2006).*
Office Action issued in corresponding Japanese Patent Application No. 2016-524104, dated Jun. 5, 2018, English portions only.
Barrett, et al., "Extraction and Measurement of Circulating Anglotensins I and II." *Clinical Chemistry*, 23(3), pp. 464-468. (1977).
Cao, et al:, "Expression of Anglotensin II and Aldosterone in Radiation-Induced Lung Injury." *Cancer Biology & Medicine*, 9(4), pp. 254-260. (2012).
Extended European Search Report issued in European Application No. 13189386.9, dated Dec. 10, 2013.
International Search Report and Written Opinion issued in International Application No. PCT/EP2014/072339, dated Dec. 4, 2014.
Kato, et al., "Responses of Plasma Norepinephrine and Renin-Angiotensin-Aldosterone System to Dynamic Exercise in Patients With Congestive Heart Failure." *Journal of Cardiac Failure*, 2(2), pp. 103-110. (1996).
Lim, et al., "The Neurohormonal Natural History of Essential Hypertension: Towards Primary or Tertiary Aldosteronism?" *Journal of Hypertension*, 20, pp. 11-15. (2002).
Lun, et al., "A Direct Radioimmunoassay for Aldosterone in Plasma,." *Clinical Chemistry*, (29(2), pp. 268-271.
McKenna, et al., "Diagnosis under Random Conditions of All Disorders of the Renin-Angiotensin-Aldosterone Axis, Including Primary Hyperaldosteronism." *Journal of Clinical Endocrinology and Metabolism*, 73(5), pp. 952-957. (1991).

(Continued)

*Primary Examiner* — Gary Counts
(74) *Attorney, Agent, or Firm* — Norton Rose Fulbright US LLP

(57) ABSTRACT

Methods and kits for the diagnosis of primary hyperaldosteronism (PHA). In particular, the present invention relates to the use of a new diagnostic parameter that is composed of the ratio between the Ang II level, in particular the steady state equilibrium Ang II level, and the aldosterone level in a biological sample, such as e.g. plasma. The ratio of the two measured parameters is used to diagnose PHA in patients and has clear advantages over currently used diagnostic methods.

28 Claims, 5 Drawing Sheets

(56) References Cited

OTHER PUBLICATIONS

Taylor, et al., "Measurement of Aldosterone in Human Plasma by Semiautomated HPLC-Tandem Mass Spectrometry." *Clinical Chemistry*, 55(6), pp. 1155-1162. (2009).

Torzewski, et al. "Animal Models of C-Reactive Protein." *Mediators of Inflammation*, pp. 1-7, (2014).

Van Der Vekiens, et al., "Human and Equine Cardiovascular Endocrinology: Beware to Compare." *Cardiovascular Endocrinology*, 2, pp. 67-76. (2013).

Wisgerhof et al., "Increased Adrenal Sensitivity to Angiotensin II in Idiopathic Hyperaldosteronism." *Journal of Clinical Endocrinology and Metabolism*, 47(5), pp. 938-943. (1978).

\* cited by examiner

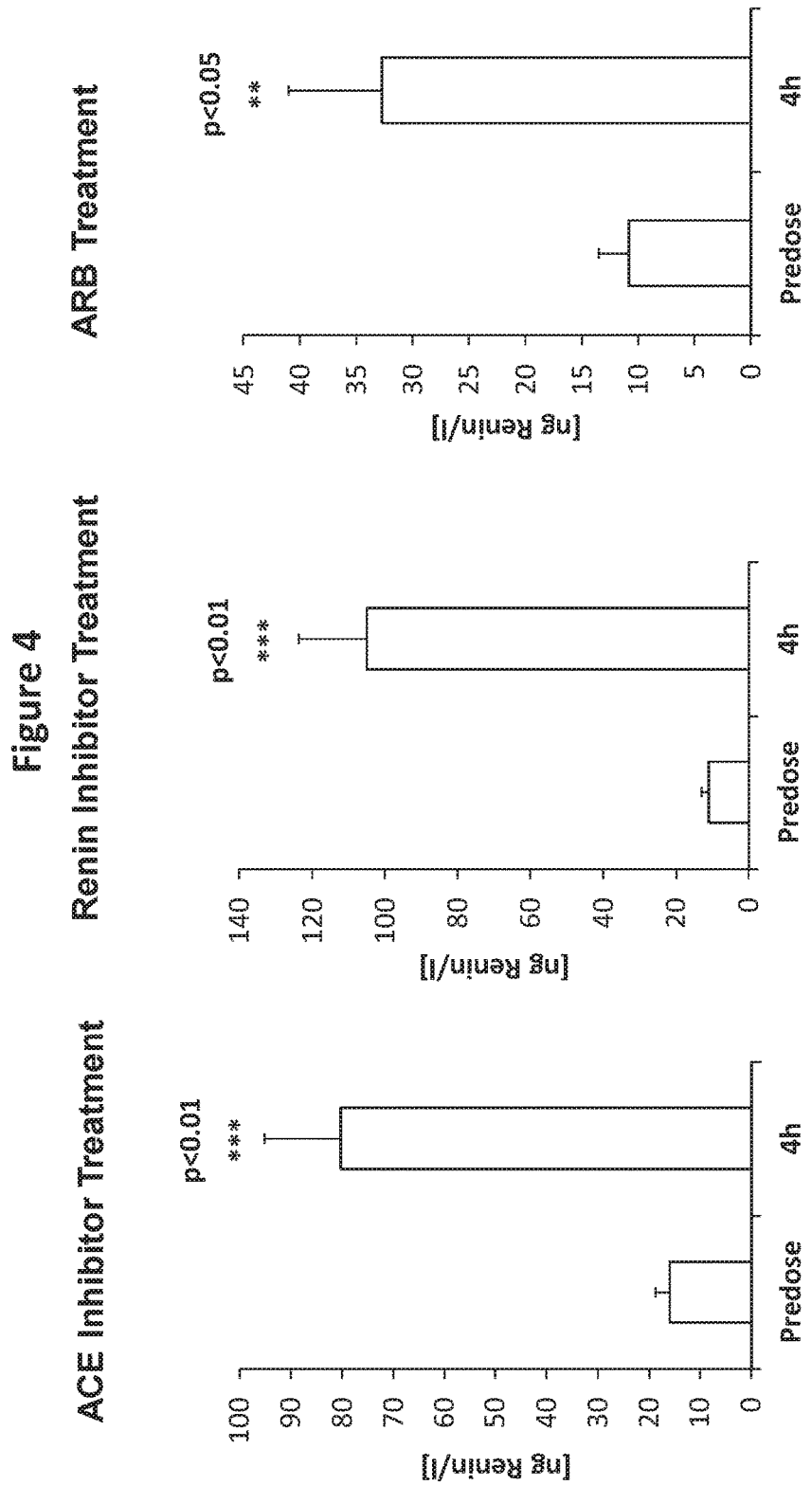

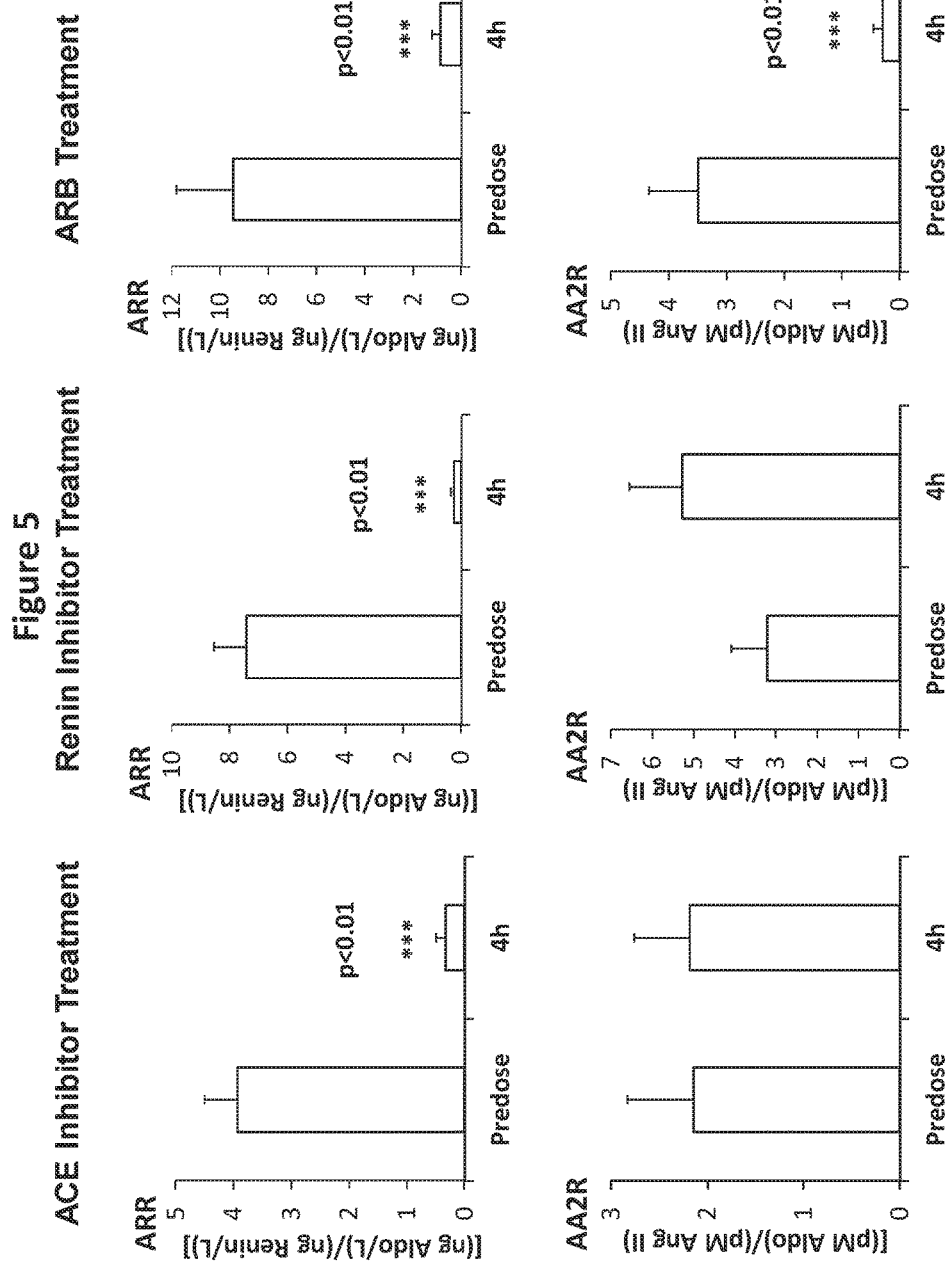

METHOD FOR DIAGNOSIS OF PRIMARY HYPERALDOSTERONISM

CROSS REFERENCE TO RELATED APPLICATIONS

This application is a continuation of U.S. patent application Ser. No. 15/030,339 filed 18 Apr. 2016, now U.S. Pat. No. 9,829,496, which is a national phase application under 35 U.S.C. § 371 of International Application No. PCT/EP2014/072339 filed 17 Oct. 2014, which claims priority to European Patent Application No. 13189386.9 filed 18 Oct. 2013 and European Patent Application No. 14152763.0 filed 28 Jan. 2014. The entire contents of each of the above-referenced disclosures is specifically incorporated by reference herein without disclaimer.

FIELD OF THE INVENTION

The present invention relates to methods and kits for the diagnosis of primary hyperaldosteronism (PHA). In particular, the present invention relates to the use of a new diagnostic parameter that is composed of the ratio between the angiotensin II (Ang II or Ang 1-8) level, in particular the steady state equilibrium Ang II level, and the aldosterone level in a biological sample, such as e.g. plasma. The ratio of the two measured parameters is used to diagnose PHA in patients and has clear advantages over currently used diagnostic methods.

BACKGROUND OF THE INVENTION

PHA, also known as primary aldosteronism, is characterized by the overproduction of the mineralocorticoid hormone aldosterone being not a result of excessive renin secretion. Aldosterone causes increase in sodium and water retention and potassium excretion in the kidneys, leading to arterial hypertension. The diagnosis of PHA in patients with arterial hypertension is a significant analytical challenge due to the interference of currently available tests with anti-hypertensive treatments and the insufficient diagnostic power of the employed assays. PHA has many causes, including adrenal hyperplasia and adrenal carcinoma. When it occurs due to a solitary aldosterone-secreting adrenal adenoma, which is a type of benign tumor and is the most frequent cause of PHA (66% of cases), it is known as Conn's syndrome. Other causes of PHA include bilateral idiopathic adrenal hyperplasia (30% of cases), primary (unilateral) adrenal hyperplasia (2% of cases), aldosterone-producing adrenocortical carcinoma (<1% of cases), familial hyperaldosteronism (FH), glucocorticoid-remediable aldosteronism (FH type I, <1% of cases), FH type II (<2% of cases) and ectopic aldosterone-producing adenoma or carcinoma (<0.1% of cases) (Williams textbook of endocrinology. (11th ed.). Philadelphia: Saunders/Elsevier. 2008. ISBN 978-1-4160-2911-3.). However, due to the limited diagnostic capabilities, data about the prevalence of subforms of PHA are divergent. Recent studies indicate that the prevalence of aldosteronism due to bilateral idiopathic adrenal hyperplasia (IAH) is higher than had previously been believed, for as many as 75% of PHA cases. Once diagnosed, PHA can be usually cured by a surgical intervention.

Measuring aldosterone alone is not considered adequate to diagnose primary hyperaldosteronism. It is known that in contrast to measuring the aldosterone levels alone, the diagnostic specificity and sensitivity for detecting PHA can be improved by measuring renin activity or concentration and aldosterone and combining the two parameters to a arithmetic ratio, the aldosterone-to-renin ratio (ARR), which is currently used for diagnosis of PHA (Tiu S, Choi C, Shek C, Ng Y, Chan F, Ng C, Kong A (2005). "The use of aldosterone-renin ratio as a diagnostic test for primary hyperaldosteronism and its test characteristics under different conditions of blood sampling". J Clin Endocrinol Metab 90 (1): 8. doi:10.1210/jc.2004-1149. PMID 15483077). The Aldosterone-to-renin ratio (ARR) is the mass concentration of aldosterone divided by the renin activity and/or renin concentration in blood plasma. The Aldosterone-to-renin ratio can be given in ng/dL per ng/(mL·h), that is, nanogram per deciliter of aldosterone per nanogram per (milliliter× hour) of renin. Also, it can be given in pmol/liter per µg/(liter·h), where aldosterone is given in molar concentration. The former can be converted to the latter by multiplying with 27.6. Also, the inverse value is occasionally given, that is, the renin-to-aldosterone ratio, the value of which is the multiplicative inverse of the aldosterone-to-renin ratio. Ratios between aldosterone and renin might also be calculated using other concentration units (mass unit per ml and/or amount unit per ml) for any of the two parameters resulting in different absolute values for the ratio while containing the similar information. The concentration of renin used for calculation of the ARR might also be given in µg UIE/ml, which is a unit frequently used in clinical diagnostics that also reflects the renin concentration.

The cutoff (or threshold) of normal individuals from those with primary hyperaldosteronism based on the ARR is significantly affected by the conditions of testing, such as body position and time of day. On average, an ARR cutoff of 23.6 ng/dL per ng/(mL·h), expressed in alternative units as 650 pmol/liter per µg/(liter·h), has been estimated to have a sensitivity of 97% and specificity of 94% (Tiu et al, cited above). An ARR value in an individual that is higher than the cutoff is used in the prior art to indicate primary hyperaldosteronism.

If the inverse ratio (i.e. renin-to-aldosterone) ratio is used, a value lower than the cutoff is considered to indicate primary hyperaldosteronism.

However, the broad range of ARR displayed by patients suffering from PHA allows no clear-cut and reliable discrimination between essential hypertension and PHA, thus leading to false-positive and/or false-negative diagnostic results and treatment decisions. Special medication and dietary requirements together with a sophisticated testing protocol involving saline infusion are required to improve the diagnostic power of the ARR in a confirmatory testing procedure subsequent to ARR screening.

It is suggested by endocrine societies to screen for PHA in patient groups at risk including patients with Joint National Commission stage 2 (>160-179/100-109 mm Hg), stage 3 (>180/110 mm Hg), or drug-resistant hypertension; hypertension and spontaneous or diuretic-induced hypokalemia; hypertension with adrenal incidentaloma; or hypertension and a family history of early-onset hypertension or cerebrovascular accident at a young age (<40 yr). Hypertensive first-degree relatives of patients with PHA show also an increased risk for PHA. According to clinical guidelines, the standard way to the diagnosis of PHA till the decision of the curing surgery is considered to be laborious and represents several risks for the patients.

The rationale behind the measurement of the ARR to diagnose PHA lies behind the physiological pathways responsible for aldosterone secretion in the adrenal cortex. Renin is a key enzyme of the renin-angiotensin-system (RAS) producing angiotensin I from angiotensinogen, which is converted to Ang II via other peptidases. Ang II is known to bind to AT1-Receptors (AT1R) leading to the secretion of aldosterone, which results in it's physiologic effects in the kidney and other tissues. Under healthy conditions, the RAS regulates plasma aldosterone levels. Under the condition of PHA, aldosterone production becomes partially independent of the RAS, meaning that renin is not further necessary to maintain aldosterone production. The measurement of the ARR tries to make use of this deregulation of renin and aldosterone. PHA patients usually have increased plasma aldosterone levels. Therefore, some investigators require elevated aldosterone levels in addition to elevated ARR for a positive screening test for PHA (usually aldosterone >15 ng/dl).

The diagnostic process for PHA is started with an ARR case detection test in patient groups specified above (John W. Funder et al.; J Clin Endocrinol Metab. September 2008, 93(9):3266-3281). In case this first measured ARR value exceeds a certain threshold, the patient is subjected to further testing in order to assure the validity of the obtained results. Of note, the exact value for the ARR threshold is still discussed in the literature, due to the frequent occurrence of false negatives and positives.

While there are few anti-hypertensive drugs that are thought to have only limited effects on the measured ARR value, many anti-hypertensive drugs are known to interfere strongly with ARR testing. The main cause of interference is represented by strong impact of these drugs on renin concentration and renin activity, leading to altered ARR results. As a consequence, a wash out phase of anti-hypertensive drugs is usually necessary before confirmation testing, which is a considerable risk for the hypertensive patients. Confirmation testing itself consists of a time consuming and cost intensive clinical procedure that is intended to reduce the renin levels of patients in response to osmotic or drug challenges in combination with ARR testing before and after the procedure.

A very common PHA confirmation test is a saline infusion test, where two liters of 0.9% saline is administered to the patient in the course of 4 hours. The volume increase should result in a decrease in renin activity and concentration. Post-test aldosterone levels below 50 pg/ml are thought to indicate the absence of PHA, while post-test aldosterone levels above 100 pg/ml are interpreted as a probable sign of PHA. Values between 50 pg/ml and 100 pg/ml are regarded to be indeterminate (John W. Funder et al.; J Clin Endocrinol Metab. September 2008, 93(9):3266-3281).

Positive confirmation testing triggers further clinical tests including adrenal imaging techniques, such as e.g. computed tomography (CT) and adrenal vein sampling (AVS) to determine the source of excessive and renin independent aldosterone production. Once the subtype is classified, unilateral adrenalectomy or treatment with mineralocorticoid receptor antagonists can be performed.

The key step in the diagnostic process is case detection in high-risk hypertensive patients. The ARR as a case detection test could easily show false positive and negative outcomes as among hypertensive patients the ARR value distribution in PHA patients was shown to overlap with the ARR value distribution of in non-PHA patients (Gary L. Schwartz and Stephen T. Turner; Clinical Chemistry 51, No. 2, 2005), which could easily lead to unnecessary mistreatment of patients. In case of false positives, these mistreatments can result in severe complications as a drug wash out phase of several weeks in a patient being hypertensive despite taking at least three anti-hypertensive drugs pose a significant risk of fatal cardiovascular events during this period of uncontrolled blood pressure. In addition to that, confirmation testing usually requires hospitalization and constant monitoring by physicians being time and money consuming for the patient and the healthcare system. In case of a false negative result, the PHA patient will continue to live with resistant hypertension, which has a fatal prognosis due to a strongly increased risk for life threatening cardiovascular events like strokes or heart attacks.

The present invention provides a method for the diagnosis of primary hyperaldosteronism in a subject, comprising obtaining a biological sample from the subject, measuring the aldosterone level and the Ang II level, and calculating the ratio thereof (aldosterone-to-angiotensin II ratio, AA2R). Said method has substantial advantages over the above described currently used ARR-based diagnostic methods.

BRIEF DESCRIPTION OF THE INVENTION

In one aspect, the present invention relates to a method for the diagnosis of primary hyperaldosteronism in a subject, comprising obtaining a biological sample from the subject, measuring the aldosterone level and the Ang II level, and calculating the ratio thereof (aldosterone-to-angiotensin II ratio, AA2R). In a second aspect, the present invention relates to a kit for diagnosing PHA, comprising an Ang II standard, an aldosterone standard, and optionally further comprising a manual and/or further components.

BRIEF DESCRIPTION OF THE FIGURES

FIG. 4: Impact of anti-hypertensive treatments on active renin concentration. Plasma samples were collected from healthy volunteers before (Predose) and 4 h post administration of a single dose of an ACE inhibitor (left), renin inhibitor (middle) or angiotensin receptor blocker (ARB, right). Mean values of 5 healthy volunteers+/−SEM are shown in the graphs.

FIG. 5: Comparison of the impact of RAS blocker administration on the ARR (upper panel) and the AA2R (lower panel). Plasma samples were collected from healthy volunteers before (Predose) and 4 h post administration of a single dose of an ACE inhibitor (left), renin inhibitor (middle) or angiotensin receptor blocker (ARB, right). Plasma aldosterone concentration, equilibrium angiotensin II concentration and active renin concentration were measured and the ARR and the AA2R was calculated for each sample. For calculation of the ARR, aldosterone concentrations in ng/L were divided by the plasma active renin concentration in ng/L. For calculation of the AA2R, aldosterone concentrations in pmol/L were divided by Ang II concentrations in pmol/L. Mean values of 5 healthy volunteers+/−SEM are shown in the graphs.

DETAILED DESCRIPTION OF THE INVENTION

Currently available methods for the diagnosis of PHA in patients make use of the correlation between plasma renin activity or plasma renin concentration and the plasma aldosterone concentration. Calculation of the aldosterone to renin ratio (ARR) was shown to allow a partial discrimination between non-PHA and PHA patients. However, false positive as well as false negative results are frequent. Renin is known to be responsible for the production of Angiotensin I (Ang I), which serves as a substrate for Ang II formation by other proteolytic enzymes like chymase or angiotensin-converting enzyme (ACE). Ang II is the main effector hormone of the RAS and is mainly responsible for RAS mediated physiologic functions including the regulation of fluid balance and blood pressure. It is widely accepted that renin activity and concentration serve as surrogate markers for the activity of the RAS (Swales J D and Thurston H J; Clin Endocrinol Metab. 1977 July; 45(1):159-63), which is used to support the use of the ARR as a diagnostic marker for PHA.

Figure 1:
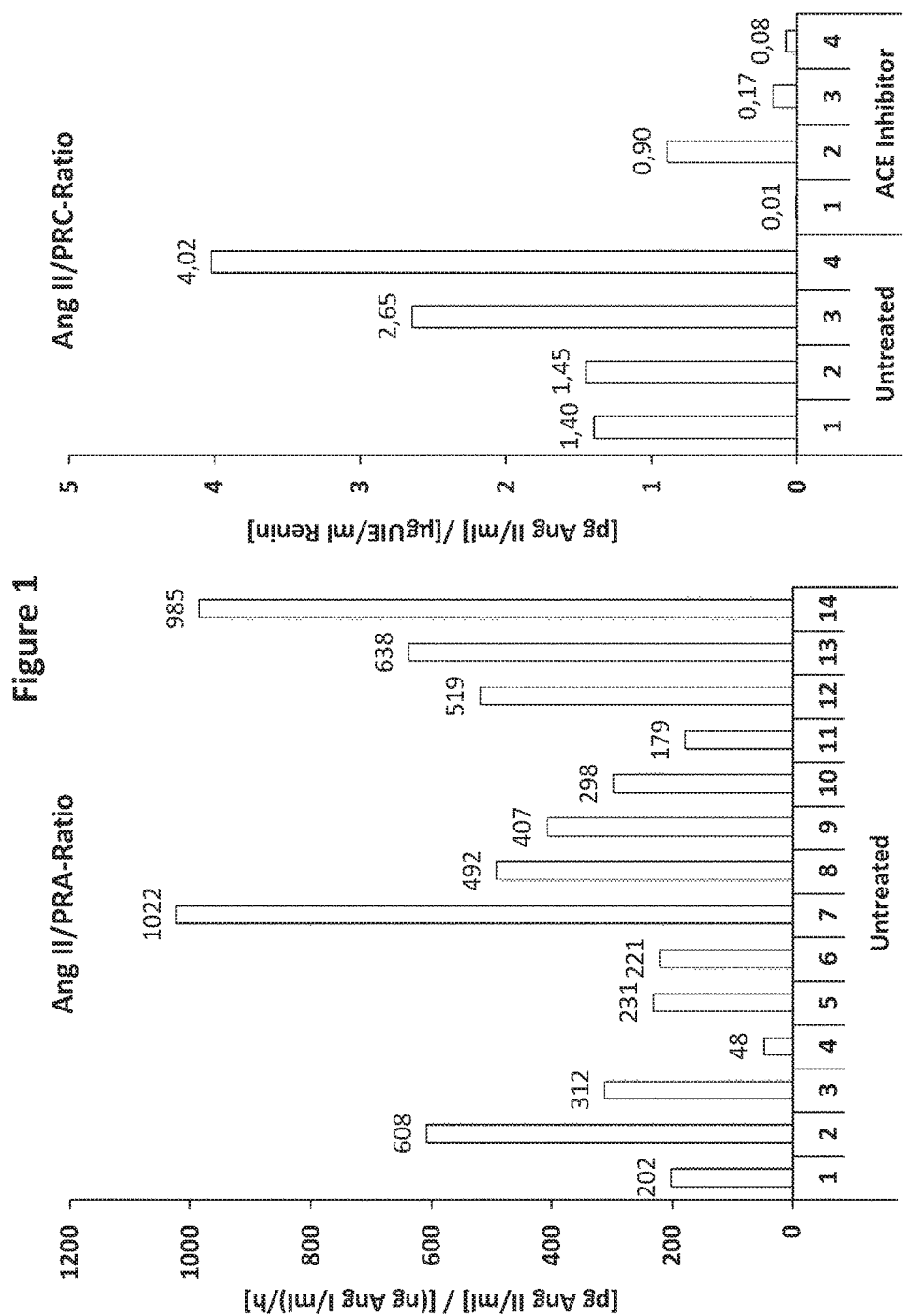
FIG. 1: Left panel: Ang II to PRA-Ratio in 14 healthy volunteers. Right panel: Ang II to PRC-Ratio in plasma of healthy untreated and ACE-Inhibitor treated healthy volunteers.

Surprisingly it turned out that Ang II levels measured in equilibrated plasma samples (i.e. Ang II levels measured according to the steady state equilibrium (SSE) method as described below, also called equilibrium Ang II levels) show a poor correlation with plasma renin activity (PRA) and plasma renin concentration (PRC), indicated by a huge variability in the Ang II to PRA and Ang II to PRC ratios when individual subjects are compared (FIG. 1, left and right panel). Blood was collected from 14 healthy volunteers without anti-hypertensive treatment. Plasma was isolated by centrifugation and equilibrium Ang II levels were measured in stabilized samples following 60 min of plasma equilibration at 37° C. The methods of measuring RAS levels in steady state equilibrium are further described in WO 2013/182237. For measurement of PRA, similar samples were subjected to an Angiotensin I formation assay as described (Bystrom et al., Clin. Chem. 56(2010), 1561-1569]). Angiotensin I was quantified by mass spectrometry and the plasma renin activity was calculated in (ng Ang I/ml)/h. The graph shows the equilibrium Ang II to renin activity ratio. The ratios of the 14 donors were in a range between 48 and 1022 [pg Ang II/ml]/[(ng Ang I/ml)/h], which is 11% and 232% of the mean of all 14 donors.

Figure 2:
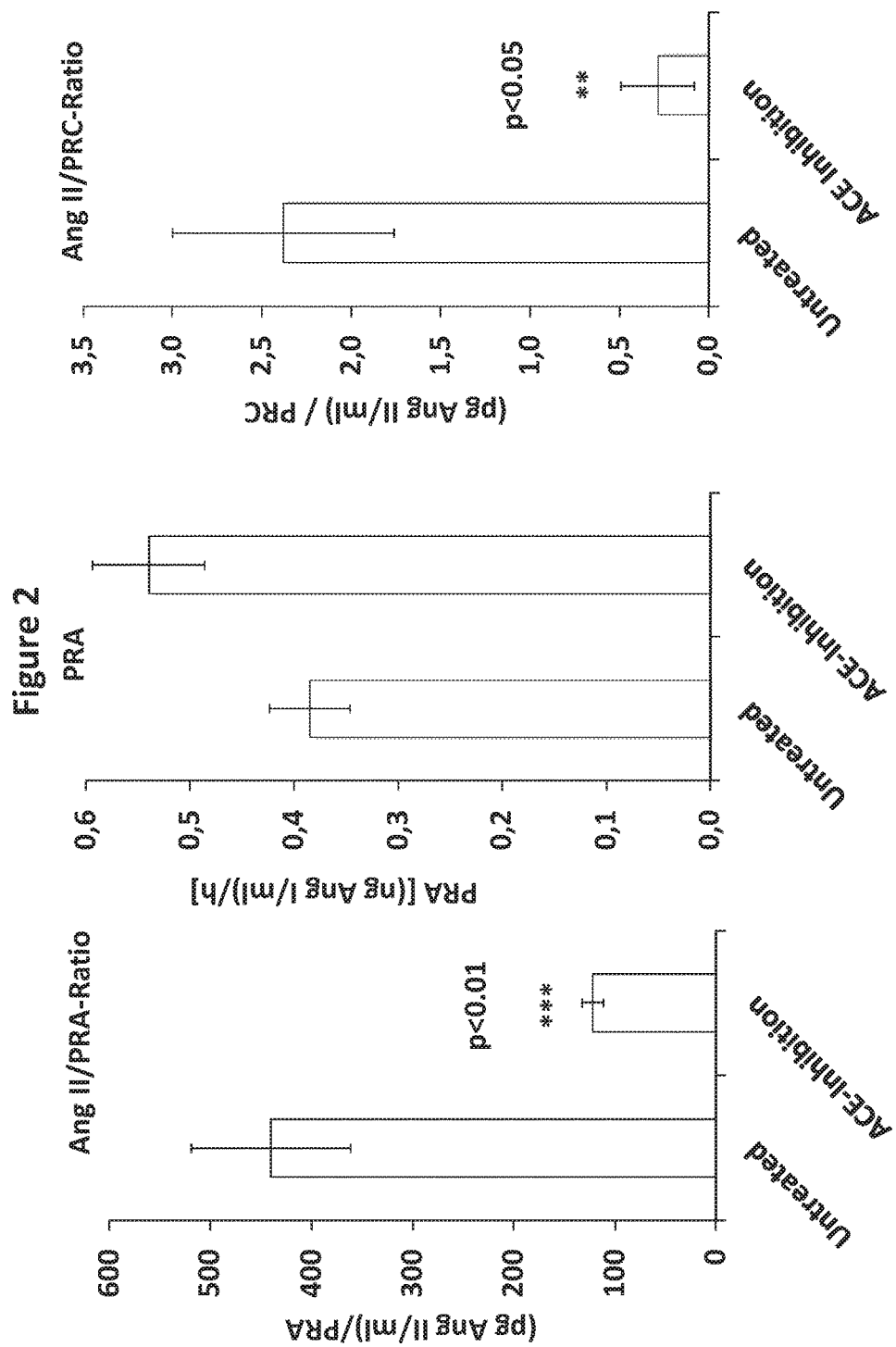
FIG. 2: Left panel: Ang II to PRA-Ratio in untreated and ACE-Inhibitor treated healthy volunteers (n=14). Middle panel: PRA in untreated and ACE-Inhibitor treated healthy volunteers (n=14). Right panel: Ang II to PRC-Ratio in untreated and ACE-Inhibitor treated healthy volunteers (n=4).

In a second approach, plasma renin concentration (PRC) was determined in 4 untreated and 4 ACE inhibitor treated volunteers using a commercially available and clinically applied antibody based renin assay (obtained from Dia-Sorin). Equilibrium Ang II levels were measured by mass spectrometry following 60 min of plasma equilibration at 37° C. and sample stabilization. The equilibrium Ang II to PRC ratio was calculated and shown in the graph for untreated and ACE inhibitor treated patients. The unit of the shown ratio is [pg Ang II/ml]/[μgUIE/ml Renin]. In all patient cohorts investigated, the Ang II to PRA and the Ang II to PRC ratio were found to be highly variable. Moreover, ACE-Inhibitor treatment resulted in a significant reduction of both the Ang II to PRC (FIG. 2, right panel) and Ang II to PRA ratios (FIG. 2, left panel).

In conclusion, a similar renin concentration and/or activity result(s) in different Ang II concentrations in individual donors indicating that renin activity and/or concentration is a poor marker for physiologic activity of the RAS. As a consequence, the ARR insufficiently displays the RAS activity related aldosterone level, putting a question mark over the suitability of the ARR as a screening tool for PHA. These considerations further explain the limitations in PHA case detection via ARR measurements, which is prone to false positive and false negative results and highly dependent on the therapeutic background of patients (John W. Funder et al.; J Clin Endocrinol Metab. September 2008, 93(9):3266-3281; and Gary L. Schwartz and Stephen T. Turner; Clinical Chemistry 51, No. 2, 2005).

Moreover Ang II to PRA and Ang II to PRC ratios are significantly affected by ACE-Inhibitor treatment (FIG. 1, right panel; FIG. 2, left and right panel). Surprisingly, while ACE-Inhibitor treatment increases renin activity and concentration, the Ang II to renin ratio was significantly reduced (FIG. 2, middle panel).

Therefore we concluded that the poor correlation of renin concentration and activity with Ang II levels in the absence and presence of an anti-hypertensive drug like an ACE-Inhibitor might cause the limited predictive power of the ARR for the diagnosis of PHA.

In contrast, the present invention relates to a method for the diagnosis of primary hyperaldosteronism in a subject, comprising measuring the aldosterone level and the angiotensin II (Ang II) level in a biological sample from the subject, and calculating the ratio between the aldosterone level and the Ang II level (aldosterone-to-angiotensin II ratio, AA2R). In one embodiment, the present invention relates to a method for the diagnosis of primary hyperaldosteronism in a subject, comprising obtaining a biological sample from the subject, measuring the aldosterone level and the angiotensin II level, and combining them to an arithmetic ratio (aldosterone-to-angiotensin II ratio, AA2R).

The term "level" as used herein refers to the concentration of a substance (e.g. a component of the RAS, such as renin, Ang II, aldosterone etc.) in a biological sample, such as e.g. blood, plasma or serum. Said concentration may be given in mol/L, mmol/ml, μg UIE/ml, ng/ml, pg/ml or any other concentration unit.

In an embodiment, a high AA2R indicates primary hyperaldosteronism and a low AA2R indicates no primary hyperaldosteronism. In an embodiment, a high AA2R as compared to the AA2R of one or more confirmed non-PHA subjects indicates primary hyperaldosteronism and/or a low AA2R as compared to the AA2R of one or more confirmed PHA subjects indicates no primary hyperaldosteronism. In an embodiment, an AA2R similar to the AA2R of one or more confirmed non-PHA patients indicates no primary hyperaldosteronism and/or an AA2R similar to the AA2R of one or more confirmed PHA patients indicates primary hyperaldosteronism. In an embodiment, the term "similar" as used above shall mean that the difference between the respective ratios (i.e. the AA2Rs) is less than 100%, 90%, 80%, 70%, 60%, 50%, 40%, 30%, 20%, 10%, or 5%.

Figure 3:
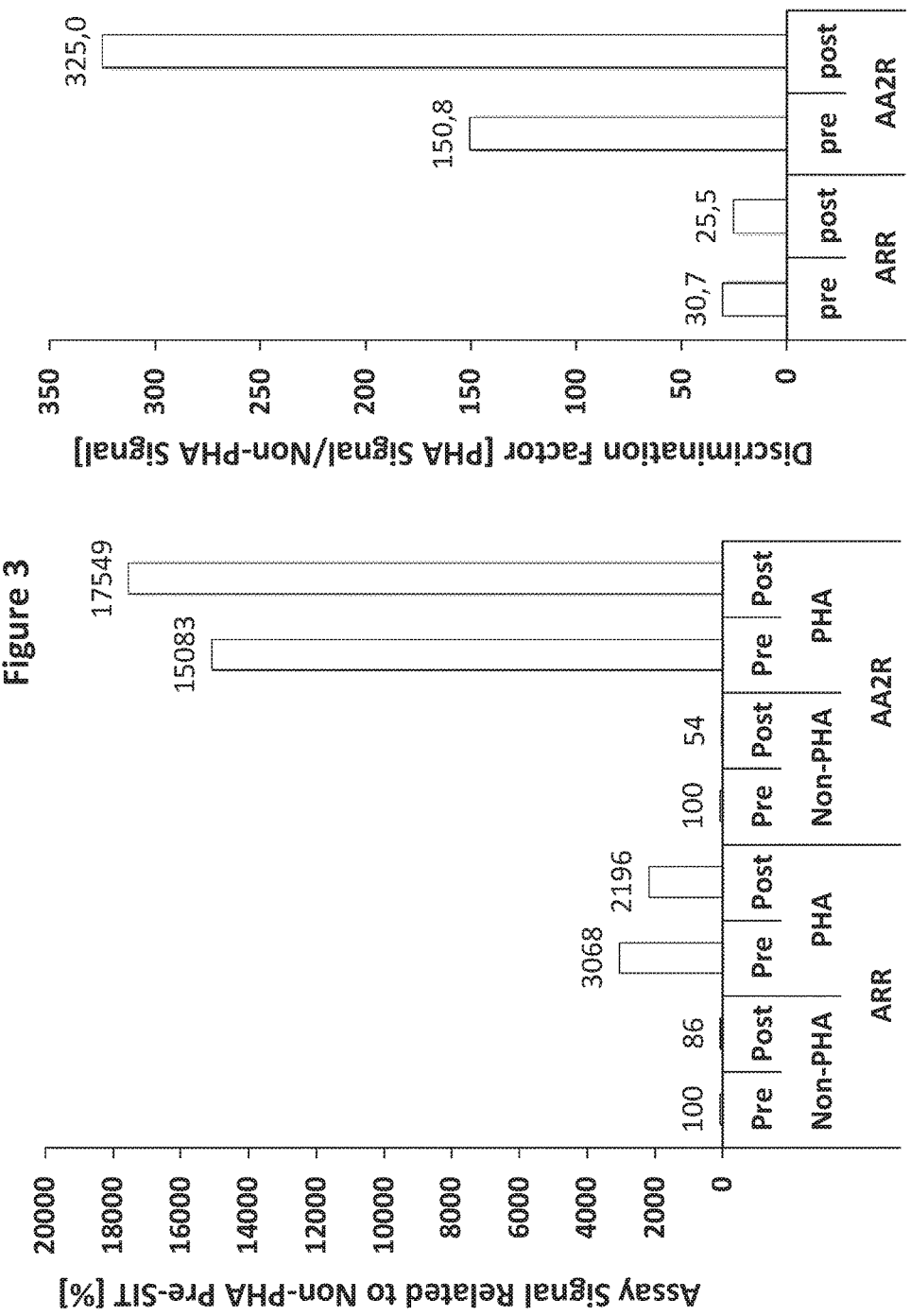
FIG. 3: Comparison of ARR and AA2R for one non-PHA patient and one confirmed PHA patient pre and post 4 h saline infusion confirmation test. Left panel: Values are given as percentage of pre infusion signal for non-PHA patient. Right panel: Comparison of ARR and AA2R specific discrimination factors between non-PHA and PHA patient are shown for each time point.

The AA2R turned out to show an improved positive to negative ratio as shown by the comparison of one non-PHA hypertensive patient with a hypertensive PHA patient pre and post a saline infusion test (SIT) (Example 1, FIG. 3). In the left panel, for each individual test (ARR and AA2R), test results were related to the pre-SIT value and expressed in percent. The PHA patient was clearly positive according to ARR test criteria, with pre and post saline infusion test (SIT) plasma aldosterone levels of 471 pg/ml and 548 pg/ml respectively, and a resulting pre and post ARR (Aldosterone to PRC ratio) of 588.8 and 421.5 respectively (PRC pre SIT: 0.8 μg UIE/ml; PRC post SIT: 1.3 μg UIE/ml). The non- PHA patient showed pre and post SIT plasma aldosterone concentration of 190 pg/ml and 64 pg/ml respectively with a pre and post SIT ARR of 19.2 and 16.4 respectively, which is clearly negative according to test criteria (John W. Funder et al.; J Clin Endocrinol Metab. September 2008, 93(9): 3266-3281). Moreover, assay specific discrimination factors were calculated as a measure of diagnostic performance (or diagnostic power) and compared for ARR and AA2R (FIG. 3, right panel). The discrimination factor is useful to compare different tests by measuring two identical samples with both tests, of which one is a true negative and one is a true positive sample. The discrimination factor represents the ratio between the true positive signal and the true negative signal. A high discrimination factor means that the difference between a true negative and a true positive sample is high, which implies a better diagnostic performance compared with a test with a lower discrimination factor obtained for similar samples. When relating the pre-SIT ARR value of the confirmed PHA patient to the pre-SIT ARR value of the confirmed non-PHA patient, a discrimination factor of 30.7 between the confirmed non-PHA patient (true negative) and the confirmed PHA patient (true positive) is obtained. The post-SIT discrimination factor between non-PHA and the PHA patient was 25.5 when analyzed by ARR.

Surprisingly, the analysis of the identical samples from the same two patients by AA2R revealed a discrimination factor of 150.8 for pre-SIT samples and a discrimination factor between the non-PHA and the PHA patient of 325.0 for post-SIT samples (FIG. 3, right panel). We conclude that using AA2R instead of ARR strongly increases the factor between negative and positive signals, leading to a markedly increased diagnostic performance.

In one embodiment of the present invention, the ratio of values between one or more confirmed PHA positive subjects and one or more confirmed PHA negative subjects (i.e. the discrimination factor) based on the AA2R is higher than between the same data sets based on the ARR. Accordingly, in an embodiment, the ratio between the AA2R of one or more confirmed PHA positive subjects and the AA2R of one or more confirmed PHA negative subjects is higher than the ratio of the same data set based on the ARR. In other words, the ratio between the AA2R of one or more confirmed PHA positive subjects and the AA2R one or more confirmed PHA negative subjects is higher than the ratio between the ARR of the same one or more confirmed PHA positive subjects and the ARR the same one or more confirmed PHA negative subjects.

The term "discrimination factor" as used herein may refer to the ratio of the diagnostic parameter (e.g. ARR or AA2R) of one or more confirmed PHA subjects (or confirmed PHA positive subjects) to the diagnostic parameter (e.g. ARR or AA2R) of one or more confirmed non-PHA subjects (or confirmed PHA negative subjects), or to one or more mean values of such parameters, e.g. a mean value of the ARR or AA2R of a cohort of confirmed PHA subjects and a mean value of the ARR or AA2R of a cohort of confirmed non-PHA subjects. Accordingly, the discrimination factor is the ratio of the ARR of one or more confirmed PHA subjects to the ARR of one or more confirmed non-PHA subjects, or the AA2R of one or more confirmed PHA subjects to the AA2R of one or more confirmed non-PHA subjects. The discrimination factor is a measure for the diagnostic performance (or diagnostic power) of the respective diagnostic parameter or test. The higher the ratio, the higher is the diagnostic power, and the lower is the risk of false positive and/or false negative results. The term "confirmed PHA subject" refers to a subject suffering from PHA and having been diagnosed as positive either by the conventional methods (e.g. a first screening test measuring the ARR, and at least one confirmation test measuring the ARR a second or third or more times, optionally prior to and after a SIT), or having been diagnosed as positive by the methods according to the present invention (e.g. the AA2R measurement not requiring any confirmation testing), and/or may even have been confirmed by surgery and/or imaging techniques (e.g. CT and/or adrenal vein sampling.) The term "confirmed non-PHA subject" refers to a subject not suffering from PHA and having been diagnosed as negative either by the conventional methods (e.g. a first screening test measuring the ARR, and optionally one or more confirmation tests measuring the ARR a second or third or more times, optionally prior to and after a SIT), or having been diagnosed as negative by the methods according to the present invention (e.g. the AA2R measurement not requiring any confirmation testing or other confirmation measures, such as e.g. imaging techniques). One or more samples from one or more "confirmed non-PHA subjects" or from one or more "confirmed PHA subjects" can be used as normal controls in the methods of the invention for comparison with the sample under investigation, i.e. one or more samples from one or more "confirmed non-PHA subjects" can be used as negative control, and/or one or more samples from one or more "confirmed PHA subjects" can be used as positive control. For example, a high AA2R as compared to the AA2R of one or more confirmed non-PHA subjects indicates primary hyperaldosteronism, and/or a low AA2R as compared to the AA2R of one or more confirmed PHA subjects indicates no primary hyperaldosteronism. If two or more samples are used as negative and/or positive control, the mean value (i.e. the arithmetic mean) or the median of the corresponding samples may be determined. Based on such control samples or values thereof, a discrimination threshold (or cutoff) may be determined, above which the subject is diagnosed to be PHA positive, and below which the subject is diagnosed to be PHA negative. Such threshold may also be determined based on the AA2R value distribution in a patient cohort comprising PHA positive and PHA negative subjects. The threshold may be determined separately for different patient cohorts (e.g. different thresholds may be determined for patient groups treated with different anti-hypertensive drugs). Any of the parameters described above that may be used to determine a threshold (or comparison level) can be used either alone or in combination with one or more of the other parameters in order to result in a final threshold.

Although the methods of the present invention may not require any confirmation testing, as already stated above, confirmation testing may nevertheless be done (e.g. if desired by a physician or patient). Furthermore, the methods of the invention itself may be used as confirmation testing, i.e. applied after a first screening test has been done with classical methods based on the ARR.

In an embodiment, the discrimination factor for one or more given data pairs or data sets (e.g. one or more suspected or confirmed PHA subjects compared to one or more suspected or confirmed non-PHA subjects, or the mean value of a cohort of suspected or confirmed PHA subjects compared to the mean value of a cohort of suspected or confirmed non-PHA subjects) as determined based on the AA2R is higher than the discrimination factor for the same data pairs or data sets as determined based on the ARR, in particular based on the ARR of a screening test (i.e. the first measurement of the ARR, and/or the ARR prior to any confirmation testing), and/or based on the ARR of a confirmation test (i.e. the second or further measurement of the ARR, and/or the ARR following any screening testing). In one embodiment, the discrimination factor for one or more given data pairs or data sets (e.g. one or more suspected or confirmed PHA subjects compared to one or more suspected or confirmed non-PHA subjects, or the mean value of a cohort of suspected or confirmed PHA subjects compared to the mean value of a cohort of suspected or confirmed non-PHA subjects) as determined based on the AA2R is higher than, in particular significantly higher than, the discrimination factor for the same data pairs or data sets as determined based on the ARR, in particular based on the ARR of a screening test (i.e. the first measurement of the ARR, and/or the ARR prior to any confirmation testing), and/or based on the ARR of a confirmation test (i.e. the second or further measurement of the ARR, and/or the ARR following any screening testing). In one embodiment, the discrimination factor for one or more given data pairs or data sets (e.g. one or more suspected or confirmed PHA subjects compared to one or more suspected or confirmed non-PHA subjects, or the mean value of a cohort of suspected or confirmed PHA subjects compared to the mean value of a cohort of suspected or confirmed non-PHA subjects) as determined based on the AA2R is at least 20%, 30%, 40%, 50%, 60%, 70%, 80%, 90%, 100%, 150%, 200%, 250%, 300%, 350%, 400%, 450%, or 500% higher than the discrimination factor for the same data pairs or data sets as determined based on the ARR, in particular based on the ARR of a screening test (i.e. the first measurement of the ARR, and/or the ARR prior to any confirmation testing), and/or based on the ARR of a confirmation test (i.e. the second or further measurement of the ARR, and/or the ARR following any screening testing). In one embodiment, the discrimination factor for one or more given data pairs or data sets (e.g. one or more suspected or confirmed PHA subjects compared to one or more suspected or confirmed non-PHA subjects, or the mean value of a cohort of suspected or confirmed PHA subjects compared to the mean value of a cohort of suspected or confirmed non-PHA subjects) as determined based on the AA2R is at least 50 percent, two-fold, three-fold, four-fold, five-fold, six-fold, seven-fold, eight-fold, nine-fold, or ten-fold higher than the discrimination factor for the same data pairs or data sets as determined based on the ARR, in particular based on the ARR of a screening test (i.e. the first measurement of the ARR, and/or the ARR prior to any confirmation testing), and/or based on the ARR of a confirmation test (i.e. the second or further measurement of the ARR, and/or the ARR following any screening testing).

The term "suspected PHA subject" refers to a subject suspected to suffering from PHA and having not yet been diagnosed as positive either by the conventional methods (e.g. a first screening test measuring the ARR, and at least one confirmation test measuring the ARR a second or third or more times, optionally prior to and after a SIT), or not having been diagnosed as positive by the methods according to the present invention (e.g. the AA2R measurement not requiring any confirmation testing), or having been diagnosed previously but with no clear outcome, and/or the previous diagnosis requiring further confirmation. The term "suspected non-PHA subject" refers to a subject suspected to not suffering from PHA and having not yet been diagnosed as negative either by the conventional methods (e.g. a first screening test measuring the ARR, and optionally one or more confirmation tests measuring the ARR a second or third or more times, optionally prior to and after a SIT), or not yet having been diagnosed as negative by the methods according to the present invention (e.g. the AA2R measurement not requiring any confirmation testing), or having been diagnosed previously but with no clear outcome, and/or the previous diagnosis requiring further confirmation.

A patient cohort might be subjected to pre-selection criteria (e.g.: minimal blood pressure, minimal aldosterone level, certain drug treatment) prior comparison of selectivity and/or sensitivity between AA2R and ARR. For example, some investigators conducting ARR based screening tests require a minimal aldosterone level of 15 ng/dl for a positive screening test result, which might result in an altered sensitivity and/or specificity compared to a non pre-selected patient cohort.

In one embodiment, the specificity of the method of the invention in a defined patient cohort is equal or higher than the specificity of the classical ARR methods in the same patient cohort, in particular based on the ARR of a screening test (i.e. the first measurement of the ARR, and/or the ARR prior to any confirmation testing). The specificity may be given in percent, wherein $$\text{specificity}[\%] = \frac{\text{number of true-negatives}}{(\text{number of true-negatives} + \text{number of false-positives})} \cdot 100$$

In one embodiment, the specificity of the method of the invention is higher than the specificity of the classical ARR methods, in particular significantly higher than the classical ARR methods. In one embodiment, the specificity is higher than 93%, 94%, 95%, 96%, 97%, 98%, or 99%. In one embodiment, the specificity of the method is at least 94%, 95%, 96%, 97%, 98%, or 99%. In one embodiment, the specificity of the method is 100%.

In one embodiment, the sensitivity of the method of the invention in a defined patient cohort is equal or higher than the sensitivity of the classical ARR methods in the same patient cohort, in particular based on the ARR of a screening test (i.e. the first measurement of the ARR, and/or the ARR prior to any confirmation testing).

The sensitivity may be given in percent, wherein $$\text{sensitivity}[\%] = \frac{\text{number of true-positives}}{(\text{number of true-positives} + \text{number of false-negatives})} \cdot 100$$

In one embodiment, the sensitivity of the method of the invention is higher than the sensitivity of the classical ARR methods, in particular significantly higher than the classical ARR methods. In one embodiment, the sensitivity of the method is at least 93%, 94%, 95%, 96%, 97%, 98%, or 99%. In one embodiment, the sensitivity of the method is higher than 93%, 94%, 95%, 96%, 97%, 98%, or 99%. In one embodiment, the sensitivity of the method is 100%.

In an embodiment, at least 90%, 91%, 92%, 93%, 94%, 95%, 96%, 97%, 98%, or 99% of all confirmed PHA subjects have a higher AA2R than at least 90%, 91%, 92%, 93%, 94%, 95%, 96%, 97%, 98%, or 99% of all confirmed non-PHA subjects. Wth the methods and kits of the present invention, it is possible to clearly differentiate between PHA and non-PHA subjects, since the degree of overlap of the AA2R value distribution of PHA and non-PHA subjects is substantially lower than the overlap of the ARR values of PHA and non-PHA subjects. In an embodiment, the overlap is 10% or less, 9% or less, 8% or less, 7% or less, 6% or less, 5% or less, 4% or less, 3% or less, 2% or less, 1% or less.

Subjects that are suspected to suffer from PHA are usually under anti-hypertensive treatment. For example, the subject has received and/or receives one or more pharmaceutical compositions (herein also referred to as drugs) or treatments, in particular anti-hypertensive pharmaceutical compositions and/or treatments, at the time the diagnosis of PHA is made. The interference of the ARR test with anti-hypertensive treatments represents a well-known obstacle for the diagnostics of PHA in hypertensive patients. Resistant hypertensive patients represent a high-risk group for PHA and are by definition treated with at least three anti-hypertensive drugs simultaneously, while still suffering from pathologically elevated blood pressure. Many of the clinically used anti-hypertensive drugs are known to have an impact on renin and aldosterone levels, while renin is usually stronger affected than aldosterone, which results in unpredictable shifts in ARR test results leading to false negative and false positive diagnostic decisions (John W. Funder et al.; J Clin Endocrinol Metab. September 2008, 93(9):3266-3281).

A widely used group of anti-hypertensive agents in clinical use is the group of RAS blockers. RAS blockers interfere with the RAS in order to either reduce the level of Ang II (e.g. Renin-Inhibitors, ACE-Inhibitors) or block the action of Ang II at the $AT_1$-Receptor (e.g. Angiotensin-Receptor-Blockers, ARBs). In addition to RAS blockers, RAS activators may be used as anti-hypertensive agents. For example, ACE2 can be administered to treat hypertension, as described e.g. in WO 2004/000367 and WO 2008/151347.

Drugs and/or treatments that affect, especially increase, renin activity and/or renin concentration affect, especially decrease, the ARR. The diagnostic power of the ARR is decreased by such drugs and/or treatments. Treatment of 5 healthy volunteers with single doses of different anti-hypertensive agents (Example 2) resulted in a highly significant, 3 to 10-fold increase in the concentration of active plasma renin (FIG. 4). These drug-induced changes in active renin concentration profoundly affected the ARR in these individuals.

The administration of a single dose of an ACE inhibitor (10 mg Enalapril), a renin inhibitor (150 mg Aliskiren) or an ARB (50 mg Losartan) resulted in a highly significant and profound decrease in the ARR (FIG. 5, upper panel), which results in a strongly reduced diagnostic power of the ARR in the presence of these anti-hypertensive drugs. Low ARR values that are caused by anti-hypertensive treatments are lead to false negative outcomes. In contrast to the ARR, most anti-hypertensive drugs did not significantly affect the AA2R, except for ARBs (FIG. 5, lower panel). The comparison of the AA2R before and after drug administration revealed that neither the administration of an ACE inhibitor, nor the administration of a renin inhibitor resulted in significant changes in the AA2R, while the ARR was significantly decreased in response to drug treatment. The ARB, that prevents the binding of Ang II to AT1 receptors therefore resulting in Ang II accumulation together with an increase in active renin concentration, was the only drug resulting in a significant decrease of the AA2R, while the ARR is significantly affected by every anti-hypertensive drug tested.

Renin activity and/or renin concentration is controlled via multiple physiologic regulatory mechanisms. Any drug that interferes with such regulatory mechanism might affect renin activity and/or concentration. For example, diuretics are a common class of anti-hypertensive drugs that reduce blood pressure by enhancing diuresis. Enhanced diuresis results in increased in renin activity and/or concentration. Therefore, the treatment of subjects with diuretics decreases the ARR. Examples for diuretics in clinical use are furosemide, torsemide, hydrochlorothiazide, azetazolamide, methazolamide, eplerenone, spironolactone, amiloride, and triamterene.

The effects on renin activity and/or concentration might also be mediated indirectly by a blockade of one or more steps in the RAS cascade that are downstream of renin.

For example, the blockade of the conversion of Ang I to Ang II by ACE inhibitors is relevant to the ARR as it results in increased renin activity and/or concentration via a physiologic compensation mechanism. This effect on renin and thus, the ARR can be also the case for other drugs interfering with enzymatic reactions of the RAS, such as the conversion of Ang I to Ang 2-10 by aminopeptidase, and/or the conversion of Ang I to Ang 1-9 by ACE2. Accordingly, one or more drugs or treatments affecting one or more of these RAS steps impair(s) the ARR-based diagnosis and lead(s) to false positive and/or false negative results. Thus, a subject to be diagnosed with ARR-based methods may not be treated with one or more such drugs or treatments.

In contrast to the ARR-based methods, the methods of the invention can also be applied to subjects that are treated with one or more of such RAS affecting drugs and/or treatments as described above, e.g. with one or more drugs or treatments that result in a decreased diagnostic power of the ARR (such as e.g. ACE inhibitors, ACE2, Renin inhibitors etc.). In particular, the methods of the invention can be applied also on subjects that are treated with agents affecting (especially increasing) the renin activity and/or concentration, i.e. the methods of the invention are independent of such treatments that affect (especially increase) the renin activity and/or concentration. In one embodiment, the subject is treated with one or more pharmaceutical compositions that decrease the diagnostic power of the ARR. In an embodiment, the subject is treated with one or more pharmaceutical compositions that decrease the diagnostic power of the ARR, and said treatment does either not decrease the diagnostic power of the AA2R or decreases the diagnostic power of the AA2R to a lesser extent.

In one embodiment, the subject is under treatment, e.g. has received and/or receives one or more pharmaceutical compositions or treatments. In one embodiment, the subject is under said treatment at the time of diagnosis, e.g. at the time the AA2R is measured and/or the sample is taken from the subject. In one embodiment, said treatment is a RAS interfering treatment, e.g. the administration of one or more RAS interfering or RAS affecting pharmaceutical compositions. In an embodiment, the subject is under anti-hypertensive treatment.

However, in one embodiment, the subject is not treated with one or more pharmaceutical compositions and/or treatments that affect the physiologic link between Ang II and aldosterone secretion (in particular the signaling via AT1 receptors), such as e.g. ARBs. Accordingly, in an embodiment of the invention, the subject is not treated with angiotensin receptor blockers (ARBs). In one embodiment, the method is independent of one or more anti-hypertensive treatments of the subject, except for treatment with angiotensin receptor blockers (ARBs).

In an embodiment, the subject is under anti-hypertensive treatment, except for ARBs. In an embodiment, the subject is under anti-hypertensive treatment, except for pharmaceutical compositions affecting the aldosterone level, but not excluding Ang II and/or renin mediated effects on the aldosterone level. In an embodiment, the subject is treated with one or more pharmaceutical compositions that increase renin concentration and/or activity. In an embodiment, the subject is under anti-hypertensive treatment, except for ARBs and except for pharmaceutical compositions affecting the aldosterone level, but not excluding compositions causing Ang II mediated effects on the aldosterone level.

In an embodiment, the terms "is/are treated with" (or "is/are not treated with") or "is under treatment with" as used herein refer to subjects (or patients) that are treated with (or are not treated with) the respective one or more drugs and/or treatments at the time of diagnosis, e.g. at the time the AA2R is measured and/or the sample is taken from the subject. Said diagnosis may be a one-step diagnosis, such as e.g. the measurement of the AA2R at one point in time, or the first diagnosis, or any further diagnosis, including confirmation testing. In a further embodiment, the subject is treated (or is not treated) with said drugs or treatments at the time of diagnosis and for a certain time period prior to diagnosis. In an embodiment, said time period is at least 1, 2, 3, 4, 5, 6, 7, 8, 9, 10, 11, 12, 13, and/or 14 days.

The term "affect" as used herein shall mean that a parameter, such as e.g. an activity, level, or ratio, is (or is not) affected, altered or changed, e.g. increased or decreased. In particular, the parameter is (or is not) substantially affected. In one embodiment, the parameter is (or is not) affected more than 10%, 20%, 30% 40%, 50%, 60%, 70%, 80%, 90%, or 100%. In one embodiment, if one parameter is affected (or not affected) more or less than another, the parameter is (or is not) at least 10%, 20%, 30%, 40% or 50%, 60%, 70%, 80%, 90%, or 100% more affected than the other. In one embodiment, the parameter is (or is not) increased more than 10%, 20%, 30% 40%, 50%, 60%, 70%, 80%, 90%, or 100%. In one embodiment, the parameter is (or is not) decreased more than 10%, 20%, 30% 40%, 50%, 60%, 70%, 80%, 90%, or 100%.

Another class of anti-hypertensive drugs or treatments that affect the ARR and/or the AA2R is represented by pharmaceutical compositions or treatments that affect (in particular substantially and/or directly affect) the aldosterone level, e.g. pharmaceutical compositions that affect the biosynthesis, half-life, and/or degradation of aldosterone, leading to altered plasma aldosterone levels. Thus, such drugs or treatments that alter the ARR and/or the AA2R via affecting the plasma aldosterone level may also be excluded from the treatment of the subject to be diagnosed with the methods of the invention. In particular, drugs or treatments that affect the AA2R in a way that the diagnostic power of the AA2R under such treatment is lower compared to the diagnostic power of the ARR under the same treatment are to be excluded from the methods according to the invention. Accordingly, in one embodiment, the subject may be treated with one or more anti-hypertensive drugs or treatments as described above, with the exception of ARBs and/or drugs that affect the aldosterone biosynthesis, half-life, and/or degradation.

Since drugs or treatments affecting Ang II (e.g. ACE inhibitors) can affect the aldosterone level, for the avoidance of doubt, it should be clarified that such drugs or treatments decreasing aldosterone via decreasing the level of Ang II and therefore, decreasing its action on AT1 receptors and resulting in diminished aldosterone secretion, need not to be excluded.

For example, therapeutic administration of the ACE inhibitor Captopril leads to a decrease in Ang II levels, while renin levels increase. Thus, ACE inhibitor treatment results in decreased aldosterone levels and increased renin activity and/or concentration. Such treatments would not substantially decrease or would even increase the diagnostic power of the AA2R, but would decrease the diagnostic power of the ARR, and thus, need not to be excluded from the methods of the invention and are actually preferred embodiments of the invention.

Only those pharmaceutical compositions and/or treatments may be excluded from the methods according to the invention, that affect or alter the AA2R in a way that the diagnostic power of the AA2R is lower compared to the diagnostic power of the ARR under similar treatment conditions (or in a way that the discrimination factor for a given data pair tested by AA2R is lower than the discrimination factor for the similar data pair tested by ARR).

Accordingly, in one embodiment, the subject is treated with one or more pharmaceutical compositions that lower the diagnostic power of the ARR, but not the diagnostic power of the AA2R, or the subject is treated with one or more pharmaceutical compositions that lower the diagnostic power of the ARR and/or of the AA2R, but in a way that the diagnostic power of the AA2R is still higher than the diagnostic power of the ARR, which may be indicated by a higher discrimination factor, specificity and/or selectivity.

The subject may or may not undergo one or more treatments, including anti-hypertensive treatments (i.e. the subject may be under treatment, e.g. anti-hypertensive treatment) at the time of diagnosis and/or prior to diagnosis. In case the diagnostic power under such a treatment is lower for the AA2R compared to the ARR, the subject might not undergo one or more such treatments, or such treatments need to be discontinued and followed by a washout phase of such treatment prior to the diagnosis based on the AA2R, as further described herein. In one embodiment, the subject to be diagnosed with the methods of the invention may be treated with one or more pharmaceutical compositions and/or treatments, except for those treatments that decrease the diagnostic power of the AA2R so that it is lower compared to the diagnostic power of the ARR under the similar treatment. In one embodiment, the method is independent of one or more treatments (especially independent of one or more anti-hypertensive treatments) of the subject, except for treatment with angiotensin receptor blockers (ARBs) and/or drugs affecting biosynthesis, half-life, and/or degradation of aldosterone.

In an embodiment, the subject to be diagnosed with the methods of the invention may be treated with one or more pharmaceutical compositions and/or treatments that do not affect aldosterone and/or Ang II. In an embodiment, the subject may be treated with one or more pharmaceutical compositions and/or treatments that do not significantly affect aldosterone and/or Ang II. In an embodiment, the subject may be treated with one or more pharmaceutical compositions and/or treatments that do not affect the AA2R. In an embodiment, the subject may be treated with one or more pharmaceutical compositions and/or treatments that do not significantly affect the AA2R. In an embodiment, the subject may be treated with one or more pharmaceutical compositions and/or treatments that affect one or more of the given parameter(s) of the AA2R (i.e. the Ang II and/or aldosterone level) and/or the ratio thereof (i.e. the AA2R) not more than 5%, 10%, 15%, or 20%. For example, the subject to be diagnosed with the methods of the invention may be treated with one or more anti-hypertensive treatments (e.g. with one or more RAS inhibitors) that alone and/or in combination result in an AA2R based discrimination factor that is (still) higher than the discrimination factor based on the ARR.

Treatment with anti-hypertensive drugs might even increase the AA2R, which could result in a shift in the discrimination threshold. In another embodiment of the present invention, the subject is treated with one or more drugs or treatments increasing the AA2R.

As described herein, one important advantage of the method of the invention is that the AA2R is much less prone to interference by anti-hypertensive treatment than the ARR. In other words, the ARR is affected (and even significantly altered) by many more anti-hypertensive drugs and/or treatments than the AA2R. Even if the AA2R might be affected by an anti-hypertensive treatment, the methods of the invention provide for an improved diagnostic power of the AA2R over the ARR under anti-hypertensive treatment, as indicated by a higher discrimination factor. Only those defined pharmaceutical compositions and/or treatments that may be excluded from an AA2R-based diagnosis (as described in the embodiments specified above) may be washed out of the blood system of the subject prior to diagnosis. Accordingly, the subject could either discontinue such medication and/or treatments, or the one or more pharmaceutical compositions and/or treatments may be replaced by other suitable pharmaceutical compositions and/or treatments, in particular other anti-hypertensive pharmaceutical compositions and/or treatments that do not (or do not significantly) affect the AA2R.

For the avoidance of doubt, if it is referred to an effect of one or more pharmaceutical compositions and/or treatments, or to one or more pharmaceutical compositions and/or treatments that affect (or do not affect) a parameter and/or ratio, it means that the effect is caused (or is not caused) either by one pharmaceutical composition or treatment alone, or by the combination of two or more pharmaceutical compositions and/or treatments, i.e. the one or more pharmaceutical compositions and/or treatments cause (or do not cause) said effect either alone, or in combination.

In one embodiment, the subject is treated with one or more drugs or treatments that alter the ARR. In an embodiment, the subject is treated with one or more pharmaceutical compositions that decrease the diagnostic power of the ARR. In an embodiment, the subject is treated with one or more pharmaceutical compositions that decrease the diagnostic power of the ARR, but do not decrease the diagnostic power of the AA2R, or decrease the diagnostic power of the AA2R to a lesser extent than the ARR. In an embodiment, the subject is treated with one or more pharmaceutical compositions that increase the diagnostic power of the ARR, but increase the diagnostic power of the AA2R to a larger extent. In an embodiment, the subject is treated with one or more pharmaceutical compositions that increase the diagnostic power of the AA2R. In an embodiment, the subject is treated with one or more pharmaceutical compositions that results in a higher diagnostic power of the AA2R compared to the diagnostic power of the ARR. In an embodiment, the subject is treated with one or more pharmaceutical compositions selected from renin inhibitors, ACE inhibitors, ACE2, diuretics and/or calcium channel blockers, or combinations thereof. In an embodiment, the subject is treated with one or more ACE inhibitors. In another embodiment, the subject is treated with one ore more renin inhibitors.

In an embodiment, the treatments and/or pharmaceutical compositions affect one or more parameter(s) of the ARR (i.e. the renin concentration and/or activity and/or the aldosterone level) and/or the ratio thereof (i.e. the ARR) more than 5%, 10%, 15%, or 20%. In an embodiment, the treatments and/or pharmaceutical compositions affect one or more parameter(s) of the ARR (i.e. the renin concentration and/or activity and/or the aldosterone level) and/or the ratio thereof (i.e. the ARR) more than 5%, 10%, 15%, or 20%, but affect the given parameter(s) of the AA2R (i.e. the Ang II and/or aldosterone level) and/or the ratio thereof (i.e. the AA2R) not more than 5%, 10%, 15%, or 20%. In one embodiment, the subject is not treated with one or more drugs or treatments that lower the discrimination factor of the AA2R as compared to the ARR. In one embodiment, the subject is treated with one or more drugs or treatments that alter the ARR, but not the AA2R.

A person skilled in the art can easily determine, whether or not a treatment affects one or both of the parameters used for diagnosis (e.g. renin level and/or renin activity, and/or aldosterone level for the ARR-based diagnosis, and Ang II and/or aldosterone level for the AA2R-based diagnosis according to the invention). For example, for many antihypertensive treatments on the market the effect(s) on the RAS and/or one or more of its components is described in the literature (see e.g. Table 4 in Funder et al., cited above). Furthermore, the effect(s) may be determined with standard methods, e.g. measuring the levels of one or more parameters in biological samples prior to and during or after treatment or comparing groups of differently treated patients using statistical methods. Alternatively or in addition, such effect(s) of a treatment may be determined by a RAS fingerprint analysis, i.e. the measurement of level(s) of one or more RAS components, especially in a steady state equilibrium, as described above and in WO 2013/182237.

The diagnostic power can be determined as described herein or in the prior art. Thus, a skilled person can easily determine the diagnostic power of the ARR and the AA2R, and compare both.

In one embodiment, the treatment comprises the administration of at least one pharmaceutical composition affecting the renin-angiotensin system (RAS), except for ARBs. In one embodiment, the treatment comprises the administration of at least one pharmaceutical composition affecting the renin-angiotensin system (RAS), except for pharmaceutical compositions affecting the aldosterone level, but not excluding Ang II mediated effects on the aldosterone level. In an embodiment, the treatment comprises the administration of at least one pharmaceutical composition affecting the renin-angiotensin system (RAS), except for ARBs and except for pharmaceutical compositions affecting the aldosterone level, but not excluding Ang II mediated effects on the aldosterone level. In an embodiment, the pharmaceutical composition affecting the renin-angiotensin system (RAS) does directly or indirectly affect (or interfere with) the RAS. In one embodiment, the pharmaceutical composition affecting (or interfering with) the renin-angiotensin system (RAS) is a composition that affects (or interfere with) the renin expression and/or activity, either directly of indirectly. Such RAS interfering drugs may comprise one or more N- or C-terminal ACE inhibitors, renin inhibitors, aminopeptidase inhibitors, and/or other compounds affecting the expression and/or secretion endogenous of RAS enzymes into the circulation. In an embodiment, the RAS affecting drugs may comprise lisinopril, capropril, aliskiren, amastatin, angiotensin converting enzyme 2 (ACE2), neutral endopeptidase, also called neprilysin (NEP), and/or other compounds affecting the expression and/or secretion of endogenous RAS enzymes, and/or combinations thereof. In an embodiment, the treatment may also comprise a specific diet, e.g. a salt-reduced diet, and/or a DASH diet (Dietary Approaches to Stop Hypertension). However, at least one of the parameters used for the current ARR-based diagnosis of PHA is often influenced by one or more of such treatments.

In contrast to the ARR, the AA2R is not affected by most of the anti-hypertensive treatments, especially RAS blocker treatment. During the treatment with RAS blockers, renin increases because of a well-known regulatory feedback mechanism induced by a lack of Ang II and leading to renin secretion. Ang II suppression further leads to decreased angiotensin dependent aldosterone secretion, which causes the AA2R to remain stable while the ARR drops due to the renin increase.

For example, ACE inhibitor treatment is associated with an increase in renin activity and concentration, which we could confirm when comparing PRA in between untreated patients and patients under ACE inhibitor (FIG. 2, middle panel). Due to an increase of renin activity and concentration in response to ACE-Inhibitor treatment, ARR is not suitable to screen patients undergoing such treatment, as the ARR is strongly decreased while renin is increased, leading to a higher number of false negative test results and therefore a decrease in assay sensitivity. As PHA screens are primarily performed in hypertensive patients, the interference with anti-hypertensive drugs is very frequent and well known (John W. Funder et al.; J Clin Endocrinol Metab. September 2008, 93(9):3266-3281). Previously explained drug interferences raise the need for confirmation tests that are designed to increase the test performance but obviously impose a significant cardiovascular risks for patients as anti-hypertensive medication has to be stopped for several weeks before the confirmation test, which leads to severe hypertension that could cause fatal cardiovascular events like stroke and heart failure.

A very common PHA confirmation test is the above described saline infusion test. The ARR test is used to confirm PHA under these defined conditions, which are intended to increase ARR assay performance and diagnostic power (John W. Funder et al.; J Clin Endocrinol Metab. September 2008, 93(9):3266-3281).

For example, usual treatments of subjects and factors or treatments that affect the ARR, i.e. the current diagnostic parameter, are described in the clinical practice guideline in Funder et al. 2008, cited above. Moreover, both the aldosterone level as well as the renin level may be affected by such treatment(s). Thus, the ARR test leads to false positive and/or false negative results resulting in inappropriate treatments. In many cases, the two parameters, i.e. the renin level and the aldosterone level, are even affected conversely, which would extremely falsify the ratio and thus, the diagnostic outcome. However, the method of the present invention is independent of such treatments, except for pharmaceutical compositions affecting the aldosterone level, but not excluding Ang II mediated effects on the aldosterone level, and except for the treatment with angiotensin receptor blockers (ARBs). This class of anti-hypertensive drugs (ARBs) directly binds to the AT1-Receptor, therefore preventing Ang II signaling. The previously explained feedback mechanism leads to increased renin concentration and activity, which results in Ang II accumulation. This would artificially lower the AA2R, which has to be considered in future PHA testing using the AA2R. However, a patient on ARB might be easily switched to another RAS blocker like an ACE-Inhibitor before measuring the AA2R. Alternatively, the one or more ARBs and/or one or more pharmaceutical compositions affecting the aldosterone level, but not excluding Ang II mediated effects on the aldosterone level (as further described above), may be washed out prior to applying the diagnostic method of the invention.

In one embodiment, the steady state equilibrium level of angiotensin II is measured. The term "steady state equilibrium" (SSE) or "SSE method" or "equilibrium level" or "equilibrium concentration" as used herein means the measurement of at least one peptidic degradation product (e.g. Ang II) of a proteolytic cascade (e.g. the RAS) in a biological sample, especially a blood sample or a blood derived sample, wherein the sample is incubated until a steady state equilibrium is reached for said at least one peptidic degradation product involved in said proteolytic cascade and wherein said at least one peptidic degradation product in a steady state equilibrium concentration (or equilibrium concentration) is quantified in the sample. In particular, the term "steady state equilibrium" (SSE) as used herein means that the actual overall degradation rate of at least one peptidic degradation product involved in the proteolytic cascade is equal to the actual overall formation rate of said peptidic degradation product, thereby leading to a stable concentration of said peptidic degradation product, i.e. a steady state equilibrium peptide concentration which does not substantially vary over a certain time period, as further specified below. In said steady state equilibrium, the actual overall formation rate of a peptidic degradation product is defined by the sum of the actual turnover rates of all enzymes involved in the formation of said peptidic degradation product, i.e. said peptidic degradation product is a direct product of said enzyme(s). The actual overall degradation rate of a peptidic degradation product is defined by the sum of the actual turnover rates of all enzymes involved in the degradation of said peptidic degradation product, i.e. said peptidic degradation product is a direct substrate of said enzyme(s). The steady state equilibrium is further described in WO 2013/182237.

The term "actual" as used herein means the actual (or effective) formation or degradation rate of a peptide, such as Ang II, or the actual or effective turnover rate of an enzyme, such as ACE, ACE2, and/or aminoepeptidase, under the conditions as present in the sample.

The term "equal to" as used herein means that the peptide concentration resulting from any such equal formation or degradation rate(s) of said peptide (the "steady state equilibrium peptide concentration" or "steady state equilibrium peptide level"), or resulting from any such equal turnover rates of at least two enzymes involved in the formation or degradation of said peptide (the "steady state equilibrium enzyme turnover rate"), does not vary more than 15%, 14%, 13%, 12%, 11%, 10%, 9%, 8%, 7%, 6%, 5%, 4%, 3%, 2%, or 1% over a time period of at least 30 minutes (min), 60 minutes, 90 minutes, 120 minutes, 150 minutes, 180 minutes, 210 minutes, 240 minutes, 270 minutes, or 300 minutes. Accordingly, the actual overall turnover rates of the enzymes involved in degradation of said peptide are determined by the actual overall formation rates of their substrate peptide(s), so that any newly or additionally formed substrate is degraded. However, this does not necessarily mean that the net concentration of said peptide is zero, but the net concentration as present in the sample in the steady state equilibrium does not significantly vary as further described above.

Accordingly, in an embodiment of the invention, the concentration of said at least one peptidic degradation product (e.g. Ang II) of the proteolytic cascade (e.g. the RAS) remains within a constant range over the time period of the steady state equilibrium, despite a continuous flow of formation and degradation. In one embodiment of the invention, the concentration of said at least one peptidic degradation product in steady state equilibrium does not vary more than 15%, 14%, 13%, 12%, 11%, 10%, 9%, 8%, 7%, 6%, 5%, 4%, 3%, 2%, or 1% over a time period of at least 30 minutes, 60 minutes, 90 minutes, 120 minutes, 150 minutes, 180 minutes, 210 minutes, 240 minutes, 270 minutes, or 300 minutes. In one embodiment, the concentration of said at least one peptidic degradation product in steady state equilibrium does not vary more than 15%, or not more than 10%, within 60 minutes. Accordingly, said peptide does neither significantly accumulate nor significantly diminish during the above specified time periods.

In an embodiment, the sample is incubated for up to 15 minutes, 20 minutes, 25 minutes, 30 minutes, 60 minutes, 90 minutes, 120 minutes, 150 minutes, 180 minutes, 210 minutes, 240 minutes, 270 minutes, or up to 300 minutes, before the at least one peptidic degradation product (in particular Ang II) in steady state equilibrium concentration is quantified in the sample. In another embodiment, the sample may be incubated for more than 6 hours (h), especially for up to 8 h, 12 h, 18 h, 24 h or up to 48 h. Suitable incubation time periods mainly dependent on the given proteolytic cascade, on the peptidic analytes to be quantified, on the nature of the sample and on the incubation parameters. Such incubation time periods can easily be determined by a person skilled in the art. In one embodiment, the steady state equilibrium is conserved (or stabilised or frozen or quenched) after incubation. The terms "conserved", "stabilised", "frozen", and "quenched" as used herein shall mean the conservation of a biochemical status, e.g. the conservation of peptide levels, e.g. by inhibition of proteolytic degradation. The stabilisation of the steady state equilibrium peptide levels (or the in vivo peptide levels) can be done by addition of one more protease inhibitors, especially by addition of a protease inhibitor cocktail. Accordingly, one or more protease inhibitors may be added after the incubation until a steady state equilibrium is reached for at least one peptidic degradation product (in particular Ang II). Suitable protease inhibitors or combinations thereof can be selected by a person skilled in the art and may e.g. comprise a combination of specific or non-specific enzyme inhibitors, or a combination thereof. The one or more protease inhibitors or the protease inhibitor cocktail ensure that especially the proteolytic steps of the cascade which are of interest (i.e. the enzymes forming and degrading the peptide to be measured, i.e. Ang II), or each enzyme of the proteolytic cascade is completely inhibited.

In one embodiment, each step of the proteolytic cascade is inhibited, i.e. each enzyme involved in the proteolytic cascade is inhibited by at least one component of the protease inhibitor cocktail. In another embodiment, the protease inhibitor cocktail comprises at least one specific or non-specific inhibitor of each class of proteases involved in the proteolytic cascade. The protease inhibitor cocktail may comprise one or more inhibitors inhibiting one or more enzymes involved in the proteolytic cascade. Examples for such inhibitors of the RAS are lisinopril (ACE inhibitor) and aliskiren (renin inhibitor). The protease inhibitor cocktail may also comprise one or more inhibitors inhibiting one or more groups of enzymes involved in the proteolytic cascade, such as e.g. Ethylenediaminetetraacetic acid (EDTA, inhibits metalloproteases). Furthermore, the protease inhibitor cocktail may comprise one or more non-specific inhibitors. In one embodiment, the protease inhibitor cocktail comprises a combination of at least two of the aforementioned classes of inhibitors. In another embodiment, the protease inhibitor cocktail comprises one or more inhibitors of the feeding enzyme, especially specific inhibitors of the feeding enzyme.

For example, at least two, at least three, or at least four protease inhibitors are added to the sample. In one embodiment, the protease inhibitor cocktail comprises Pepstatin A, 1,10-Phenanthroline, EDTA, p-Hydroxymercuri-benzoic acid and the renin inhibitor peptide Z-Arg-Arg-Pro-Phe-His-Sta-Ile-His-Lys (Z-Arg).

Alternatively, or in addition to the use of one or more protease inhibitors or a protease inhibitor cocktail, the steady state equilibrium may be conserved by the addition of one or more chaotropic agents, such as sodium iodide, sodium perchlorate, lithium perchlorate, magnesium chloride, guanidine thiocyanate (GTC), guanidinium chloride, phenol, propanol, butanol, ethanol, sodium dodecyl sulfate, thiourea, urea or others.

Alternatively, or in addition to the use of one or more protease inhibitors or a protease inhibitor cocktail, the steady state equilibrium may be conserved by other means of physical inactivation of the enzymes in the sample, for example, denaturation of the enzyme induced by heat, salt, pH, or detergent; or by cooling, e.g. placing the samples on ice directly after incubation. For one or more of the further processing steps of the samples, e.g. the plasma or serum separation and the separation by solid phase extraction (SPE; e.g. for matrix depletion and/or peptide enrichment), an according ambient temperature can be selected as well to ensure that all enzymes in the sample are inactive. For example, any sample pre-treatment or sample processing prior to sample analysis may be done at 4° C. ambient temperature (or lower), at least up to the complete denaturation or inactivation of the enzymes involved in the proteolytic cascade (e.g. until eluation from the SPE column or cartridge).

In contrast, classical plasma renin assays (PRA) are aimed on complete inhibition of the degradation pathways of angiotensin I (Ang I) immediately after the sample has been taken, and the enzyme activity is calculated based on the accumulation rate of the peptide formed by said enzyme. Even if the inhibition of the Ang I degradation pathways may be incomplete in such PRA assays, they are still far from any steady state equilibrium according to the invention, since the net concentration of Ang I significantly changes over time. In the PRA assay as described e.g. in Bystrom et al. (Clin. Chem. 56 (2010), 1561-1569), the Ang I concentration significantly increases over time. Moreover, state-of-the-art assays are seeking to assess the overall activity of the RAS by measuring the conformational activated form of renin in plasma samples by enzyme-linked immunosorbent assay (ELISA) and radioimmunoassay (RIA) based methods (DRG Diagnostics). In contrast to the SSE measurements as described above, these assays critically depend on the specificity of the used antibody and allow no conclusions about the concentration of the effector peptides in the samples, which are responsible for the physiologic effects of the RAS. The reason for that is that there exist multiple enzymes affecting the level of effector peptides. All these peptides may be simultaneously analysed by SSE measurements while state-of-the-art assays focus on just one enzyme activity or concentration per sample.

In an embodiment of the invention, in the steady state equilibrium, the actual turnover rate of the feeding enzyme is maximal, i.e. the feeding substrate is present in vast molar excess compared to the feeding enzyme, and any addition of external feeding substrate would not further increase the actual turnover rate of the feeding enzyme. Accordingly, the feeding enzyme of a proteolytic cascade is the enzyme, which is responsible for the feeding conversion reaction, i.e. the rate-limiting step of the subsequent proteolytic cascade (or the bottleneck of the proteolytic cascade). For the RAS proteolytic cascade under physiologic conditions, the feeding enzyme is renin, which is responsible for the conversion of angiotensinogen to angiotensin I. In physiological systems (e.g. in the body, in blood, plasma or serum samples), angiotensinogen as the substrate for renin is present in vast molar excess of renin. However, in one embodiment of the invention, one or more, or all other enzymes of the RAS proteolytic cascade, such as e.g. aminopeptidases (AP), especially aminopeptidase A (APA) and/or aminopeptidase N (APN), dipeptidyl aminopeptidases (DAP), carboxypeptidases (especially ACE2), dipeptidyl carboxypeptidases (especially ACE), and/or endopeptidases (especially neutral endopeptidase, also called neprilysin), are present in the sample at concentrations sufficient to degrade any newly or additionally formed substrate and thus, allow the establishment of a steady state equilibrium for said enzymes and peptide(s) during incubation, i.e. their actual overall turnover rates are determined by the actual overall formation rates of their substrate peptide(s).

According to the present invention, the term "feeding enzyme" shall mean an enzyme with a maximal actual turnover rate, i.e. with an actual turnover rate that is the maximal achievable turnover rate for said enzyme in the sample. The term "maximal achievable turnover rate" shall mean the turnover rate of an enzyme contained in the sample, which can be achieved under the given conditions in the sample, if the substrate peptide is (or would be) present in vast molar excess compared to the enzyme (or a virtually inexhaustible amount) at least until the steady state equilibrium is reached. Accordingly, the actual turnover rate of the feeding enzyme cannot be further increased by the addition of external substrate, since the feeding substrate is already present in vast molar excess compared to the feeding enzyme. If, for example, any external substrate peptide (i.e. a peptide involved in the proteolytic cascade) or an analogue of such substrate is added to a sample before or during the incubation until a steady state equilibrium is reached, this may—according to the present definition—result in a change of the rate-limiting step(s) for the proteolytic cascade, and thus, also of the feeding enzyme(s) of the proteolytic cascade, if the amount of added substrate peptide is sufficient to result in a maximal achievable turnover rate of at least one enzyme involved in the degradation of said substrate peptide (i.e. an enzyme other than the feeding enzyme under physiologic conditions). For example, if the proteolytic cascade under investigation is the RAS, and if a vast molar excess of an Ang II (or an analogue thereof, e.g. a Ang II carrying a mass label or a any covalent modification including amino acid exchanges) compared to one or more or all enzymes involved in Ang II degradation is added to the sample before or during incubation until a steady state equilibrium is reached, at least one or even all enzymes involved in the degradation of Ang Ang II (e.g. ACE2, AP, and/or DAP) would reach maximal achievable turnover rates and thus, would become the rate-limiting feeding step(s) for the subsequent proteolytic reaction(s) of the cascade.

In an embodiment of the invention, feeding enzyme may be added to the sample. The addition of feeding enzyme increases the flow-through of the enzyme cascade and thus, leads to in-creased absolute levels of peptides, while the relative levels (peptide ratios) remain unchanged. Accordingly, the steady state equilibrium levels of the one or more peptides still reflect the physiological situation, i.e. the enzyme activities, however, the overall peptide levels are increased proportionally. This would be useful, for example, if the peptide levels measured without the addition of feeding enzyme would be below the detection limit of the method used to quantify the peptide(s). Optionally, feeding substrate may be added as well. This may ensure that feeding substrate is and remains in molar excess compared to the feeding enzyme and that feeding substrate is still present in virtually inexhaustible amounts leading to a turnover rate of the feeding enzyme, which is stable for a certain time defining the steady state equilibrium, even if feeding enzyme is added.

In one embodiment, the proteolytic cascade is the RAS, and the peptide to be analysed is Ang II. In said embodiment, the actual turnover rate of said Ang II degrading enzyme in the steady state equilibrium is equal to the actual turnover rate of ACE, which is the Ang II forming enzyme, if only one enzymatic Ang II degradation pathway is "open" in the sample, i.e. only one Ang II degrading enzyme is active. If more than one Ang II degradation enzymes are active in the sample, the sum of the actual turnover rates of said active Ang II degrading enzymes (i.e. the actual overall degradation rate of Ang II) is equal to the actual turnover rate of ACE (i.e. the actual overall Ang II formation rate) in said embodiment.

Accordingly, a steady state equilibrium is reached for the peptide, e.g. Ang II, and the related enzyme(s), i.e. the enzyme(s) forming or degrading said peptide (e.g. Ang II). As described above, the steady state equilibrium is reached, if the net concentration of the at least one peptide (in particular Ang II), two or more peptides, or all peptides involved in the proteolytic cascade, does not vary more than 15%, 14%, 13%, 12%, 11%, 10%, 9%, 8%, 7%, 6%, 5%, 4%, 3%, 2%, or 1% over a time period of at least 30 minutes, 60 minutes, 90 minutes, 120 minutes, 150 minutes, 180 minutes, 210 minutes, 240 minutes, 270 minutes, or 300 minutes. Said steady state equilibrium is reached after incubation of the sample for 15 minutes, 20 minutes, 25 minutes, 30 minutes, 60 minutes, 90 minutes, 120 minutes, 150 minutes, 180 minutes, 210 minutes, 240 minutes, 270 minutes, or 300 minutes, or for 8, 12, 18, 24, or 48 h. The steady state equilibrium continues for at least 30 minutes, 60 minutes, 90 minutes, 120 minutes, 150 minutes, 180 minutes, 210 minutes, 240 minutes, 270 minutes, or 300 minutes.

In an embodiment of the invention, in the steady state equilibrium the overall maximal achievable degradation rate of at least one peptide involved in the proteolytic cascade (e.g. Ang II) is equal to or higher than its actual overall formation rate. According to the invention, the maximal achievable degradation rate of a peptide is the overall degradation rate which could be achieved under the given conditions in the presence of a vast molar excess of said peptide compared to each enzyme degrading said pep-tide (or a virtually inexhaustible amount of said peptide), i.e. by addition of external peptide. Accordingly, the maximal achievable degradation rate of a peptide is the sum of maximal achievable turnover rates of all enzymes involved in the degradation of said peptide.

In one embodiment, at the start of the incubation time the amount of all enzymes involved in the proteolytic cascade is in excess of the amount of their respective substrate(s), except for the feeding enzyme of the proteolytic cascade. In another embodiment, the amount of said one or more enzymes or of all enzymes involved in the proteolytic cascade is in excess of the amount of its/their respective substrate(s) during the entire time period of incubation, except for the feeding enzyme of the proteolytic cascade.

In another embodiment, the conditions as specified above (i.e. that the amount of enzyme is in excess of the amount of the respective substrate, and/or that the rate of formation of a peptide is equal to the rate of degradation in steady state equilibrium) apply at least to the one or more peptides to be analysed (e.g. Ang II), and/or the respective enzyme(s) which form or degrade said peptide(s) to be analysed (e,g, Ang II).

For example, if the SSE method of the present invention is used to examine a component of the RAS proteolytic cascade, and the peptide to be analysed is Ang II, this means that until a steady state equilibrium is reached, the actual rate of formation of Ang II by ACE is higher than the sum of the actual degradation rates of all enzymes involved in Ang II degradation, including but not limited to ACE2, AP, and/or DAP. Accordingly, the Ang II concentration increases, i.e. Ang II accumulates, until a steady state equilibrium is reached. When the steady state equilibrium is reached, the actual rate of formation of Ang II is equal to the sum of the actual turnover rates of all enzymes involved in Ang II degradation (the actual overall degradation rate of Ang II).

Accordingly, in an embodiment of the steady state equilibrium of the present invention, at least one proteolytic degradation reaction has to be active or "open" for the peptide to be analysed, e.g. Ang II, to an extent which allows that the actual overall degradation rate is equal to the actual overall formation rate of said peptide, i.e. is not inhibited or "closed", e.g. by use of one or more protease inhibitors, to an extent that the actual overall formation rate exceeds the actual or maximum achievable overall degradation rate of the said peptide.

In one embodiment, chelating agents, such as e.g. EDTA, ethylene glycol tetraacetic acid (EGTA), 8-hydroxyquinoline, phenanthroline and dimercaprol (also called British-anti-Lewisite or BAL), are not added before and/or during the incubation until a steady state equilibrium is reached, especially not for the RAS cascade or other proteolytic cascades where metalloproteases are involved, since chelating agents have an inhibitory effect on metalloproteases through chelating of bivalent ions.

In one embodiment, chaotropic agents, such as e.g. sodium iodide, sodium perchlorate, lithium perchlorate, magnesium chloride, guanidine thiocyanate (GTC), guanidinium chloride, phenol, propanol, butanol, ethanol, sodium dodecyl sulfate, thiourea, urea, and/or others, are not added before and/or during the incubation until a steady state equilibrium is reached.

In one embodiment, the steady state equilibrium is reached under physiological conditions for said proteolytic cascade, which means that the components of the proteolytic cascade (enzymes and substrate or product peptides), their total and/or relative amounts as present in the biological sample as taken from the body, as well as the matrix in respect to composition and/or pH of the sample are not or not substantially modified before and/or during the incubation until a steady state equilibrium is reached. In one embodiment, the concentrations of the enzymes and/or peptides involved in the proteolytic cascade present in the biological sample as taken from the body are not modified before and/or during the incubation until a steady state equilibrium is reached.

In another embodiment, substrates or substrate analogues of any enzyme(s) involved in the proteolytic cascade, such as e.g. internal standards or degradation standards, whether in their native form or modified by labeling (e.g. isotopic and/or fluorescent labeling, and/or amino acid modifications or exchanges of at least one amino acid), are not added before and/or during the incubation until a steady state equilibrium is reached. In one embodiment of the present invention, the proteolytic cascade is the RAS, and neither angiotensinogen, angiotensin I and/or Ang II, nor any analogues thereof, are added before and/or during the incubation until a steady state equilibrium is reached.

In another embodiment, further substances or reagents, such as e.g. buffer substances (Tris, PBS, MES, HEPES, citrate, borate, carbonate or hydrogen carbonate (or bicarbonate) and/or other buffer substances or respective buffer solutions are not added before and/or during the incubation until a steady state equilibrium is reached.

In still another embodiment, substances or reagents, such as e.g. EDTA, EGTA, PMSF, AEBSF, BSA, maleic acid, maleic anhydride, formic acid, and/or water (in any form, e.g. de-ionised and/or distilled etc.) are not added before and/or during the incubation until a steady state equilibrium is reached.

However, and notwithstanding the foregoing, one or more such afore mentioned protease inhibitors, chelating agents, chaotropic agents, substrates, standards, BSA, buffers, and/or other substances or reagents may be added once the steady state equilibrium is reached and optionally quenched.

Especially, one or more standards, e.g. internal standards and/or degradation standards, may be added once a steady state equilibrium is reached and frozen. Standards are, for example, peptides of the proteolytic cascade, which are modified by mass labeling and/or chemical labeling (e.g. isotopic and/or fluorescent labeling, and/or amino acid modifications, and ore the use of mass tags, and/or exchanges of at least one amino acid). Accordingly, internal standards are stable isotope labeled internal standards, e.g. disclosed in WO 03/016861 A. In one embodiment, the biological sample is incubated as taken from the subject (ex vivo), i.e. the matrix of the sample and/or the concentrations of the components of the proteolytic cascade to be analysed are not modified, but optionally further processed (e.g. to obtain plasma or serum), either before or after a steady state equilibrium is reached and stabilised. Optionally, anti-coagulants, i.e. substances, which prevent coagulation (stopping blood from clotting), may be added to the biological sample before and/or during incubation until a steady state equilibrium is reached. However, such anti-coagulants should not substantially affect the proteases of the proteolytic cascade to be analysed. A suitable anti-coagulant for use in the SSE method according to the present invention is heparin.

Prior to analysis, the samples may be pre-treated or further processed, e.g. by plasma or serum separation (e.g. by centrifugation or activation of coagulation followed by centrifugation), and/or purification by solid phase extraction (SPE), e.g. for matrix depletion and/or peptide enrichment. Accordingly, the solid phase extraction may be carried out with a reversed phase chromatography material, a hydrophobic interaction chromatography material, an ion exchange material, affinity chromatography material, e.g. a reversed phase chromatography material, especially a C18, C8 or C6H5 (Phenyl) material.

In one embodiment, the one or more analyte(s) (e.g. Ang II) is/are concentrated to dryness after eluting from the solid surface and may be reconstituted in a high pressure liquid chromatography (also called high performance liquid chromatography, HPLC) compatible solvent, meaning that the composition of the solvent does not interfere with binding of the one or more analytes to the MS coupled HPLC column. The reconstitution solvent is e.g. an aqueous solvent which might be supplemented with additives including propanol, butanol, 2-butanol, pentanol, 2-propanol, acetone, methyl ethyl ketone, acetonitrile, methanol, ethanol, acids or bases in order to enhance solubility of analytes and/or facilitate binding of analytes to the HPLC column.

In another embodiment, the SSE methods according to the invention comprise the steps: providing a sample treated with an anti-coagulant; optionally, further processing the sample to obtain a plasma or serum sample; incubating the sample until a steady state equilibrium is reached for at least one peptidic degradation product involved in the proteolytic cascade; conserving said steady state equilibrium; optionally, adding one or more internal standard(s) once the steady state equilibrium is conserved; conducting a solid phase extraction with the sample; and analysing the sample. The plasma or serum separation may be done either prior to or after the step of incubation until a steady state equilibrium is reached (and optionally stabilised), depending on whether the steady state equilibrium is to be investigated in plasma, serum, or whole blood.

The analysis of the at least one peptidic degradation product, optionally in steady state equilibrium concentration, or the aldosterone level may be done e.g. by mass spectrometry (MS); by liquid chromatography, such as high pressure liquid chromatography (also called high performance liquid chromatography, HPLC); especially by liquid chromatography-electrospray ionisation-mass spectrometry (LC-MS), and/or liquid chromatography-tandem mass spectrometry (LC-MS/MS). For example, Cui et al. (Anal Biochem. 369 (2007), 27-33) disclose liquid chromatography-electrospray ionisation-mass spectrometry and liquid chromatography tandem mass spectrometry methods for quantifying angiotensin peptides. For each peptide or analyte and corresponding internal standards, different mass transitions can be measured. The performance of the method may be monitored using quality control samples.

Such quality control samples may include, for example, biological samples with pre-defined analyte concentrations, as well as synthetic samples comprising a mixture of pre-defined concentrations of synthetic peptides. For example, the quality control sample may be a pooled blood, plasma, or serum sample or pooled tissue homogenate sample with pre-defined concentrations of one or more peptides. Angiotensin peptide concentrations (e.g. the Ang II concentration) may be calculated by relating endogenous peptide signals to internal standard signals provided that integrated signals achieved a signal-to-noise ratio above 10.

Furthermore, the analysis may be done by radio immune assay (RIA) or enzyme linked immunosorbent assay (ELISA). Optionally, a HPLC purification step may be done prior to the RIA or ELISA based quantification of peptidic degradation products of the proteolytic cascade.

In one embodiment, the sample pre-treatment, sample processing, and/or the analysis of the samples may be done in a multiwell format, e.g. on 96 well plates.

A steady state equilibrium concentration of a peptide (e.g. Ang II) in that context means that its rate of formation is equal to its rate of degradation leading to a peptide (e.g. Ang II) concentration, which does not substantially or significantly change over time for a certain period of time, and which is strongly dependent on affinities of the enzymes to their substrates under the given conditions rather than maximal enzyme conversion rates, as further described above. Since the present invention deals with biological systems, it is clear that the term "steady state equilibrium" cannot be regarded as a single point to be reached, but more as a kinetic target region of peptide concentrations, which do not significantly change over time for a certain period of time. More accurate time periods until such steady state equilibrium concentrations are reached are mainly dependent on the given proteolytic cascade, on the peptidic analytes to be quantified, on the nature of the sample and on the incubation parameters. This can easily be determined for each cascade. In general, the "steady state equilibrium window" wherein the quantification according to the present invention can be performed is rather large, at least for some of the proteolytic cascades, especially those in blood. Usually, the steady state equilibrium is reached after a certain incubation time, which is empirically determined (e.g. 30 minutes for the RAS system) and then stays stable for an extended period of time (e.g. 6 hours (h) for the RAS system). Then, the steady state equilibrium is disturbed by effects such as degradation and inactivation of the involved en-zymes or a lack of feeding substrate in the sample. The feeding substrate concentration based time of stability (ts) for a given cascade can be calculated by dividing the concentration of the feeding substrate (or feeding precursor peptide) (cf) reduced by an enzyme- and sample-specific constant defining the minimal substrate concentration to achieve the maximal turnover rate of the feeding enzyme in the sample (cmin), by the turnover rate of the feeding enzyme of the cascade, thereby defining the feed rate (Vf) of the cascade.

$$t_S = (c_f - c_{min})/V_f$$

$t_S$ feeding substrate concentration based time of stability [h]
$c_f$ feeding substrate concentration [mol/L]
$c_{min}$ sample specific minimal substrate concentration to achieve the maximal turnover rate of the feeding enzyme in the sample [mol/L]
$V_f$ feed rate of the cascade [[mol/L]/[h]]
and $$c_{min} = f \cdot c_E$$

f excess factor
$c_E$ feeding enzyme concentration

For example, the application of these formulas above on the RAS, where the feeding conversion is carried out by renin, yields a calculated feeding substrate concentration based time of stability of the RAS steady state equilibrium of about 60 to 200 hours based on different published values for PRA (plasma renin activity, PRC (plasma renin concentration), see e.g. [Nishiyama et al. 2010, and Bystrom et al., Clin. Chem. 56 (2010), 1561-1569], and applying a AGT concentration of e.g. 70 µg/ml plasma and an excess factor of e.g. 1000. Of course, said calculated feeding substrate concentration based time of stability should serve as a rough and theoretic reference point only, since the actual time of stability of the steady state equilibrium may differ significantly in the samples.

In contrast to state-of-the-art methods, where inhibitors are used to immediately stabilise peptides produced by certain enzymes with limited success [Bystrom et al., Clin. Chem. 56 (2010), 1561-1569], according to the present invention the sample is allowed to reach an enzyme activity defined steady state equilibrium for at least one peptide involved in the proteolytic cascade, e.g. Ang II. This innovative approach allows a highly re-producible assessment of Ang II in the physiological sample matrix while integrating enzyme activities involved in the metabolism of Ang II. Another advantage over state-of-the-art technologies is that substrate concentrations in the assay according to the present invention generally remain below the concentration of metabolising enzymes (except for the feeding enzyme), taking into consideration the affinity of the enzyme for each single substrate under the given conditions in the sample (e.g. physiologic conditions) in contrast to in vitro enzyme activity assays, where this important feature is neglected for means of simplification by using excess amounts of substrate.

Specifically for blood samples, it is important for reaching the steady state equilibrium for at least one peptide involved in the proteolytic cascade (e.g. Ang II), that the proteases of the proteolytic cascade to be observed with the present SSE method are not inhibited by addition of protease inhibitors to the sample, at least not to an extend which does not allow at least one enzyme involved in the degradation of said at least one peptide to work until the steady state is reached for said at least one peptide, i.e. at least one degradation enzyme of said peptide(s) has to be active to an extend to allow steady state equilibrium for said peptide(s). Therefore, in one embodiment, protease inhibitors are not added to the sample to an extent, that the activities of the proteases involved in the formation and degradation of the at least one peptide to be analysed (e.g. Ang II) are significantly inhibited, before and/or during the incubation until a steady state equilibrium is reached. According to said embodiment, the samples are not combined with such protease inhibitors or, if such inhibitors have already been added, such inhibitors are inhibited (in their protease inhibiting function) or removed before and/or during the incubation until a steady state equilibrium is reached. Of course, inhibitors which do not affect the proteases of the relevant proteolytic cascade which should be studied by the SSE method according to the present invention, but which inhibit other proteolytic activities (e.g. inhibitors of blood coagulation if the RAS is studied), can be added to the sample, because this would not affect the ability of the relevant proteolytic cascade (i.e. the cascade to be analysed, e.g. the RAS) to reach a steady state equilibrium for at least one peptide of the cascade.

It is advantageous to quantify the one or more proteolytic degradation products (e.g. Ang II) in the steady state equilibrium. This is essentially different from prior art analyses, which usually apply quantification of analytes in a status of the proteolytic cascade immediately stabilised after the samples (i.e. blood samples) are taken from the subjects, i.e. not in a steady state equilibrium. Usually, such prior art samples have been treated with protease inhibitors immediately after taking of the samples in order to inhibit unwanted enzyme dependent changes in the cascade. The SSE method, however, uses such enzyme dependent changes in analysing the physiologic or biochemical status of the subject concerning the proteolytic cascade by specifically allowing the proteases of said cascade under investigation to perform their proteolytic activity until a steady state equilibrium is reached. This will usually lead to a change in the amount and composition of the peptidic degradation products in the proteolytic cascade under investigation compared to the sample immediately stabilised after the taking of the sample from the subject. The sample specific proteolytic activity leads to a steady state equilibrium which is much more indicative of the biochemical status of the subject concerning this cascade than the immediately stabilised sample (without the incubation step until a steady state equilibrium is reached).

As already indicated above, the steady state equilibrium according to the present invention is not a single, quantitatively exactly determined and isolated point, but a status where changes in the relative ratios have been substantially reduced in the sample. Usually, such a steady state equilibrium can be reached by applying usual incubation conditions for the given samples and the cascade under investigation. As specified above, the sample may be incubated for up to 15 minutes, 20 minutes, 25 minutes, 30 minutes, 60 minutes, 90 minutes, 120 minutes, 150 minutes, 180 minutes, 210 minutes, 240 minutes, 270 minutes, or 300 minutes. For the RAS and/or the bradykinin system, the samples may be incubated for at least 30 min to up to 300 min, or for at least 30 min to up to 180 min, or for at least 30 min to up to 120 min, or for at least 30 min to up to 90 min, or for at least 30 min to up to 60 min. Suitable incubation temperatures are those present in the physiologic system or those, wherein the proteases of the proteolytic cascade under investigation have their optimal temperature of action, e.g. at a temperature of 30 to 50° C., 35 to 40° C., or especially of about 37° C. (specifically for human blood or blood derived samples).

Since the SSE method according to the present invention applies the proteolytic activities contained in the sample, the one or more samples, especially blood samples, should be free of added protease inhibitors for the proteolytic cascade before the steady state equilibrium is reached.

Such protease inhibitors may be added after the incubation until a steady state equilibrium is reached and stabilised. This safeguards that the peptide concentration(s) (in particular the Ang II concentration) reflecting the steady state equilibrium is/are still present during the quantification step (although the steady state equilibrium is usually stable over a certain period of time, this provides additional quality assurance for the SSE method).

The SSE method is dependent on an exact and accurate quantification of the peptidic degradation products. Since many samples, especially blood samples contain proteins, salts, acids, bases, lipids, phospholipids or other components, which can disturb peptide quantification; methods for pre-treatment of the samples before quantification may be applied.

In one embodiment, the subject is a subject suffering from hypertension, and/or is resistant to antihypertensive treatment, and/or is suspected to suffer from PHA, and/or is in need for a PHA positive or negative diagnosis. In one embodiment, the subject is a human. In an embodiment, the subject is an animal, e.g. a cat, dog, horse, rat, mouse, rabbit, pig and/or cattle.

As described above, the methods of the prior art usually comprise one screening phase, in which the ARR is determined once, followed by confirmation testing, in which the ARR or aldosterone alone is determined at least a second time until PHA can be diagnosed with sufficient sensitivity and specificity. The reason for this strategy is the frequent occurrence of false positive results. The above described saline infusion confirmation test would even comprise the determination of the ARR three times (once at screening, a second time in confirmation testing prior to saline infusion, and a third time after saline infusion). In contrast, the methods of the present invention allow a diagnosis based on one test or step, e.g. the measurement of the AA2R only once.

Accordingly, in one embodiment, the method is a one-step diagnosis. In an embodiment, the diagnosis comprises only one measurement of the AA2R (at one point in time). In one embodiment, the angiotensin II level and/or the aldosterone level is measured only once.

In an embodiment, said one-step diagnosis leads to a confirmed diagnosis. In an embodiment, said one-step diagnosis does not require confirmation testing, such as e.g. any second or further measurement of the AA2R or other parameters. In one embodiment, no saline infusion test is required.

In an embodiment, the biological sample is a blood sample or a blood derived sample. For example, the blood sample or blood derived sample is whole blood, serum, EDTA plasma, heparin plasma, citrate plasma, heparin blood, EDTA blood, or citrate blood. In one embodiment, at least one of the levels is measured by mass spectrometry. In one embodiment, at least one of the levels is measured by antibody based quantification methods, such as e.g. ELISA. In one embodiment, both levels are measured by mass spectrometry. In one embodiment, both levels are measured by antibody based quantification methods. This can be easily done, as kits for both individual analytes are commercially available. However, mass spectrometry has significant advantages over antibody based quantification methods regarding selectivity and reproducibility.

In another aspect, the present invention relates to a kit for diagnosing PHA, comprising an angiotensin II standard, and an aldosterone standard.

In an embodiment, the kit may further comprise a manual, one or more solvents, one or more detergents, and/or one or more solid phase extraction cartridges.

In one embodiment, the manual comprises a description of the method according to the invention, in particular, a description of any of the above described embodiments of the method. In an embodiment, the kit comprises an isotope labeled angiotensin II standard and/or an isotope labeled aldosterone standard. In an embodiment, the kit comprises an angiotensin II antibody and/or an aldosterone antibody.

The invention is further exemplified by the following embodiments, which can be readily combined with any one of claims 1 to 15:

1. A method for the diagnosis of primary hyperaldosteronism in a subject, comprising measuring the aldosterone level and the Ang II level, and combining them to an arithmetic ratio (aldosterone-to-ang II-ratio, AA2R) or a method as defined in the claims, especially claim 1.
2. The method of embodiment 1, wherein a high AA2R indicates primary hyperaldosteronism and a low AA2R indicates no primary hyperaldosteronism.
3. The method of embodiment 1 or 2, wherein the discrimination factor based on the AA2R of a given data pair or data set is higher than the discrimination factor based on the ARR of the same data pair or data set.
4. The method of any of embodiments 1 to 3, wherein the specificity of the method is higher than 93%, 94%, 95%, 96%, 97%, 98% or 99%.
5. The method of any of the preceding embodiments, wherein the sensitivity of the method is at least 93%, 94%, 95%, 96%, 97%, 98%, or 99%.
6. The method of any of the preceding embodiments, wherein at least 95% of all confirmed PHA subjects have a higher AA2R than at least 95% of all confirmed non-PHA subjects.
7. The method of any of the preceding embodiments, wherein said method is independent of any treatment of the subject, except for ARBs and except for pharmaceutical compositions affecting the aldosterone level, but not excluding Ang II mediated effects on the aldosterone level.
8. The method of embodiment 7, wherein said treatment is a RAS interfering treatment.
9. The method of any of the preceding embodiments, wherein the steady state equilibrium level of angiotensin II is measured.
10. The method of any of the preceding embodiments, wherein the subject is a human.
11. The method of any of the preceding embodiments, wherein the subject is under anti-hypertensive treatment, except for ARBs and except for pharmaceutical compositions affecting the aldosterone level, but not excluding Ang II mediated effects on the aldosterone level.
12. The method of embodiment 11, wherein said treatment comprises the administration of at least one pharmaceutical composition affecting the renin-angiotensin system (RAS).
13. The method of any of the preceding embodiments, wherein the method is a one-step diagnosis and does not require any confirmation testing.
14. The method of any of the preceding embodiments, wherein the levels are measured only once.
15. The method of any of the preceding embodiments, wherein no saline infusion test is required.
16. The method of any of the preceding embodiments, wherein the biological sample is a blood sample or a blood derived sample.
17. The method of any of the preceding embodiments, wherein the blood sample or blood derived sample is whole blood, serum, plasma, heparin blood, EDTA blood, or citrate blood.
18. The method of any of the preceding embodiments, wherein at least one of the levels is measured by mass spectrometry.
19. The method of any of the preceding embodiments, wherein at least one of the levels is measured by antibody based quantification methods.
20. A kit for diagnosing PHA, comprising an angiotensin II standard, an aldosterone standard, and a manual.
21. The kit of embodiment 20, further comprising one or more solvents, detergents, and/or solid phase extraction cartridges.
22. The kit of embodiment 20 or 21, wherein the manual comprises a description of the method according to any of embodiments 1 to 19.
23. The kit of any of embodiments 20 to 22, wherein the kit is for a mass spectrometry quantification method of at least one level and comprises an isotope labeled angiotensin II standard and/or an isotope labeled aldosterone standard.
24. The kit of any of embodiments 20 to 23, wherein the kit is for an antibody based quantification method of at least one level and comprises an angiotensin II antibody and/or an aldosterone antibody.

EXAMPLES

Example 1: Measurement of AA2R in Plasma of Hypertensive Patients

Saline Infusion Test (SIT) and Sample Collection

One non-PHA patient and one PHA patient were subjected to SIT. Patients underwent SIT according to endocrine society guidelines (John W. Funder et al.; J Clin Endocrinol Metab. September 2008, 93(9):3266-3281). Briefly, two liters of 0.9% saline was administered to the patient in the course of 4 hours (Saline infusion test, SIT). EDTA blood and heparin blood samples were taken before (pre-SIT) and after (post-SIT) the 4 h saline infusion. Blood samples were centrifuged in a cooled centrifuge at 3000 g for 10 min and frozen at −80° C. until analysis by mass spectrometry.

Measurement of Equilibrium Ang II Levels

Equilibrium Ang II levels were determined by quantification of the steady-state angiotensin peptide levels in equilibrated heparin plasma samples. Therefore, thawed heparin plasma samples were incubated for 30 min at 37° C. in a water bath. Following equilibration, plasma angiotensin peptide levels were stabilized by the addition of protease inhibitors and equilibrium peptide levels were subsequently quantified by mass spectrometry. Therefore, stable isotope-labeled Ang II was added to the stabilized plasma samples at a concentration of 200 pg/ml for internal standardization. Following C18-based solid-phase-extraction, samples were subjected to mass spectrometry analysis using a reversed-phase analytical column (Acquity UPLC® C18, Waters) operating in line with a XEVO TQ-S triple quadrupole mass spectrometer (Waters) in MRM mode. Two different mass transitions were measured per analyte and standard and the concentrations were calculated by relating endogenous signals to internal standard signals under consideration of the corresponding response factors determined by calibration curves in human blank plasma.

Measurement of Plasma Aldosterone Levels

Stable isotope-labeled aldosterone was added to the stabilized plasma samples at a concentration of 500 pg/ml for internal standardization. Following C18-based solid-phase-extraction, samples were subjected to mass spectrometry analysis using a reversed-phase analytical column (Acquity UPLC® C18, Waters) operating in line with a XEVO TQ-S triple quadrupole mass spectrometer (Waters) in MRM mode. Two different mass transitions were measured per analyte and standard and the concentrations were calculated by relating endogenous signals to internal standard signals under consideration of the corresponding response factors determined by calibration curves in human blank plasma.

Calculation

Obtained concentrations of aldosterone were divided by the obtained concentrations for Ang II in each plasma sample.

Example 2: Measurement of the AA2R in Healthy Volunteers Receiving Different Anti-Hypertensive Treatments Treatments and Sample Collection Single doses of three different anti-hypertensive drugs were administered to 5 healthy volunteers on 3 different treatment days separated by one week. 4 h following administration of a single dose of 10 mg Enalapril (ACE-Inhibitor), 50 mg Losartan (ARB) or 150 mg Aliskiren (Renin-Inhibitor), heparin blood was collected by venous puncture and plasma was separated by centrifugation. Samples were frozen at −80° C. till analysis.

Measurement of Equilibrium Ang II Levels

Equilibrium Ang II levels were determined by quantification of the steady-state angiotensin peptide levels in equilibrated heparin plasma samples. Therefore, thawed heparin plasma samples were incubated for 60 min at 37° C. in a water bath. Following equilibration, plasma angiotensin peptide levels were stabilized by the addition of protease inhibitors and equilibrium peptide levels were subsequently quantified by mass spectrometry. Therefore, stable isotope-labeled Ang II was added to the stabilized plasma samples at a concentration of 200 pg/ml for internal standardization. Following C18-based solid-phase-extraction, samples were subjected to mass spectrometry analysis using a reversed-phase analytical column (Acquity UPLC® C18, Waters) operating in line with a XEVO TQ-S triple quadrupole mass spectrometer (Waters) in MRM mode. Two different mass transitions were measured per analyte and standard and the concentrations were calculated by relating endogenous signals to internal standard signals under consideration of the corresponding response factors determined by calibration curves in human blank plasma.

Measurement of Plasma Aldosterone Levels

StSable isotope-labeled aldosterone was added to the stabilized plasma samples at a concentration of 500 pg/ml for internal standardization. Following C18-based solid-phase-extraction, samples were subjected to mass spectrometry analysis using a reversed-phase analytical column (Acquity UPLC® C18, Waters) operating in line with a XEVO TQ-S triple quadrupole mass spectrometer (Waters) in MRM mode. Two different mass transitions were measured per analyte and standard and the concentrations were calculated by relating endogenous signals to internal standard signals under consideration of the corresponding response factors determined by calibration curves in human blank plasma.

The invention claimed is:

1. A method for indicating primary hyperaldosteronism (PHA) in a human subject, comprising:
   incubating a blood sample or blood derived sample ex vivo until a steady state equilibrium is reached for angiotensin II, in which the actual overall degradation rate of angiotensin II is equal to the actual overall formation rate of angiotensin II;
   measuring an aldosterone level and the angiotensin II (Ang II) level in the same sample from the human subject; and
   calculating a ratio between the aldosterone level and the Ang II level (aldosterone-to-angiotensin II-ratio, AA2R), wherein an AA2R which is higher than an AA2R of one or more confirmed non-PHA human subjects indicates primary hyperaldosteronism and/or an AA2R which is lower than an AA2R of one or more confirmed PHA human subjects indicates no primary hyperaldosteronism.

2. The method of claim 1, wherein the ratio of values between one or more confirmed PHA positive human subjects and one or more confirmed PHA negative human subjects based on the AA2R is higher than between the same data sets based on the aldosterone to renin ratio (ARR).

3. The method of claim 1, wherein the specificity and/or sensitivity of the method is higher than the specificity and/or the sensitivity of the AAR in the same patient cohort.

4. The method of claim 1, wherein the blood sample or blood derived sample is from a subject that is under anti-hypertensive treatment.

5. The method of claim 1, further comprising treating the human subject with at least one pharmaceutical composition that increases renin concentration and/or activity.

6. The method of claim 1, further comprising treating the human subject with at least one pharmaceutical composition that decreases the test sensitivity and/or specificity of the aldosterone to renin ratio (ARR).

7. The method of claim 4, wherein said treatment does either not decrease the sensitivity and/or specificity of the AA2R, or decreases the sensitivity and/or specificity of the AAR more than the sensitivity and/or specificity of the AA2R.

8. The method of claim 6, wherein the one or more pharmaceutical composition comprises a renin inhibitor, an ACE inhibitor, ACE2, a diurectic, or a calcium channel blocker.

9. The method of claim 1, wherein the human subject is not treated with angiotensin receptor blockers (ARBs).

10. The method of claim 1, wherein the sample is whole blood, plasma, or serum.

11. The method of claim 1, wherein at least one of the levels is measured by mass spectrometry.

12. The method of claim 1, wherein at least one of the levels is measured by antibody based quantification methods.

13. The method of claim 1, wherein
the AA2R is compared to two or more AA2R values of confirmed non-PHA human subjects and to two or more AA2R values of confirmed PHA human subjects; and
a threshold is determined based on the AA2R value distribution in a patient cohort comprising confirmed non-PHA human subjects and on the AA2R value distribution in a patient cohort comprising confirmed PHA human subjects; and
the human subject is diagnosed to be PHA positive if the AA2R value is above the threshold or wherein the human subject is diagnosed to be PHA negative if the AA2R value is below the threshold.

14. The method of claim 13, wherein the specificity and/or the sensitivity of the method is higher than the specificity and/or the sensitivity of the ARR in the same patient cohort.

15. A method for obtaining an aldosterone-to-angiotensin II-ratio (AA2R), comprising:
measuring an aldosterone level and an angiotensin II (Ang II) level in a blood sample or blood derived sample from a human subject wherein:
the sample is incubated ex vivo until a steady state equilibrium is reached for angiotensin II, in which the actual overall degradation rate of angiotensin II is equal to the actual overall formation rate of angiotensin II; said steady state equilibrium is conserved by adding at least one protease inhibitor; and/or at least one chaotropic agent; and/or by denaturation by heat, salt, pH or detergent; and/or by cooling; and
the angiotensin II level is measured in the steady state equilibrium; and
calculating a ratio between the aldosterone level and the Ang II level (aldosterone-to-angiotensin II-ratio, AA2R).

16. The method of claim 15, wherein the ratio of values between one or more confirmed PHA positive human subjects and one or more confirmed PHA negative human subjects based on the AA2R is higher than between same data sets based on an aldosterone to renin ratio (ARR).

17. The method of claim 15, wherein the specificity and/or the sensitivity of the method is higher than the specificity and/or the sensitivity of the AAR in the same patient cohort.

18. The method of claim 15, wherein the human subject is under anti-hypertensive treatment.

19. The method of claim 18, wherein treatment either does not decrease the sensitivity and/or specificity of the AA2R, or decreases the sensitivity and/or specificity of the ARR more than the sensitivity and/or specificity of the AA2R.

20. The method of claim 15, further comprising treating the human subject with at least one pharmaceutical composition that increases renin concentration and/or activity.

21. The method of claim 15, further comprising treating the human subject with at least one pharmaceutical composition that decreases the test sensitivity and/or specificity of the aldosterone to renin ratio (ARR).

22. The method of claim 21, wherein the one or more pharmaceutical composition comprises a renin inhibitor, an ACE inhibitor, ACE2, a diuretic, or a calcium channel blocker.

23. The method of claim 15, wherein the human subject is not treated with angiotensin receptor blockers (ARBs).

24. The method of claim 15, wherein the sample is whole blood, plasma, or serum.

25. The method of claim 15, wherein at least one of the levels is measured by mass spectrometry.

26. The method of claim 15, wherein at least one of the levels is measured by antibody-based quantification methods.

27. The method of claim 15, wherein
the AA2R is compared to two or more AA2R values of confirmed non-PHA human subjects and to two or more AA2R values of confirmed PHA human subjects; and
a threshold is determined based on the AA2R value distribution in a patient cohort comprising confirmed non-PHA human subjects and on the AA2R value distribution in a patient cohort comprising confirmed PHA human subjects; and
the human subject is diagnosed to be PHA positive if the AA2R value is above the threshold or wherein the human subject is diagnosed to be PHA negative if the AA2R value is below the threshold.

28. The method of claim 26, wherein the specificity and/or the sensitivity of the method is higher than the specificity and/or the sensitivity of the ARR in the same patient cohort.

* * * * *